United States Patent
Zhou et al.

(10) Patent No.: US 11,267,079 B2
(45) Date of Patent: Mar. 8, 2022

(54) METHODS AND SYSTEMS FOR CUTTING OR PERFORATING A WEB WITH A LASER

(71) Applicant: Kimberly-Clark Worldwide, Inc., Neenah, WI (US)

(72) Inventors: Peiguang Zhou, Cumming, GA (US); Paul Milbrodt, Neenah, WI (US); Wade R. Thompson, Cumming, GA (US); Vikram S. Kaul, Atlanta, GA (US); Wen Yuan, Randolph, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 16/634,343

(22) PCT Filed: Aug. 28, 2019

(86) PCT No.: PCT/US2019/048541
§ 371 (c)(1),
(2) Date: Jan. 27, 2020

(87) PCT Pub. No.: WO2020/047073
PCT Pub. Date: Mar. 5, 2020

(65) Prior Publication Data
US 2020/0384575 A1 Dec. 10, 2020

Related U.S. Application Data

(60) Provisional application No. 62/725,434, filed on Aug. 31, 2018.

(51) Int. Cl.
*B23K 26/38* (2014.01)
*B23K 26/60* (2014.01)
(Continued)

(52) U.S. Cl.
CPC ........ *B23K 26/38* (2013.01); *A61F 13/15723* (2013.01); *B23K 26/60* (2015.10); *B23K 2103/30* (2018.08)

(58) Field of Classification Search
CPC .... B23K 26/38; B23K 26/60; B23K 2103/30; A61F 13/15723
See application file for complete search history.

(56) References Cited

U.S. PATENT DOCUMENTS 3,870,593 A * 3/1975 Elton .......................... C09J 7/26
602/58
5,670,225 A 9/1997 Yamanaka et al.
(Continued)

FOREIGN PATENT DOCUMENTS

| JP | 2003227062 A * | 8/2003 |
|---|---|---|
| KR | 20170080545 A | 7/2017 |
| WO | 14208652 A1 | 12/2014 |

OTHER PUBLICATIONS

Machine translation of Japan Patent document No. 2003-227,062, May 2021.*

(Continued)

*Primary Examiner* — Geoffrey S Evans
(74) *Attorney, Agent, or Firm* — Kimberly-Clark Worldwide, Inc.

(57) ABSTRACT

Methods and systems for cutting or perforating webs are disclosed. A method of cutting or perforating a web can include providing a web including a film. The film can include a polyolefin polymer and a plurality of particles. The film can include a width and length defining a surface. The method can further include stretching the film to provide a stretched film. Stretching the film can provide a plurality of voids in the stretched film. The method can additionally include providing a laser assembly. The method can include (Continued)

directing a beam of light from the laser assembly upon the surface of the web to cut or perforate the web in at least one location.

19 Claims, 17 Drawing Sheets

(51) Int. Cl.
*A61F 13/15* (2006.01)
*B23K 103/00* (2006.01)

(56) References Cited

U.S. PATENT DOCUMENTS

| | | | |
|---|---|---|---|
| 6,075,179 A | 6/2000 | McCormack et al. | |
| 7,041,381 B1 | 5/2006 | Rasp et al. | |
| 7,303,642 B2 | 12/2007 | Topolkaraev | |
| 9,566,666 B2 | 2/2017 | Pacetti et al. | |
| 9,895,819 B1 | 2/2018 | Aminpour | |
| 2003/0179687 A1* | 9/2003 | Schoeppel | G11B 7/256 369/273 |
| 2008/0085397 A1 | 4/2008 | Asai et al. | |
| 2008/0107879 A1 | 5/2008 | Kliesch et al. | |
| 2008/0107880 A1* | 5/2008 | Kliesch | B32B 27/20 428/212 |
| 2008/0141839 A1* | 6/2008 | Van Gompel | A61F 13/15593 83/39 |
| 2010/0108494 A1* | 5/2010 | McClure | B01D 67/0086 204/192.11 |
| 2010/0276505 A1* | 11/2010 | Smith | B23K 26/40 239/8 |
| 2011/0152815 A1* | 6/2011 | Wang | A61F 13/51401 604/385.01 |
| 2012/0179125 A1 | 7/2012 | Kanya et al. | |
| 2013/0102982 A1* | 4/2013 | Nakano | A61F 13/49019 604/365 |
| 2015/0037535 A1* | 2/2015 | Akimoto | C09C 1/3072 428/141 |
| 2016/0185087 A1* | 6/2016 | Kian | C08K 3/36 264/400 |
| 2016/0263705 A1* | 9/2016 | Kim | B23K 26/0622 |
| 2016/0361780 A1* | 12/2016 | Miller | B23K 26/38 |
| 2017/0120389 A1 | 5/2017 | Lee et al. | |
| 2017/0182695 A1* | 6/2017 | Hanschen | B01J 20/28033 |
| 2017/0189242 A1* | 7/2017 | Piantoni | B23K 26/03 |

OTHER PUBLICATIONS

Heston, Tim, "Laser cutting on the level, How flat metal can remain flat after laser cutting", The Fabricator, Apr. 3, 2014, https://www.thefabricator.com/article/lasercutting/laser-cutting-on-the-level.

* cited by examiner

US 11,267,079 B2

METHODS AND SYSTEMS FOR CUTTING OR PERFORATING A WEB WITH A LASER

TECHNICAL FIELD

The present disclosure relates to methods and systems for cutting or perforating a web with a laser. More specifically, the present disclosure relates to methods and systems for cutting or perforating a web including a film with particles with a laser. The present disclosure also relates to such webs including such a film.

BACKGROUND OF THE DISCLOSURE

Laser cutting technology provides a non-contact, flexible cutting system that is used in a variety of manufacturing applications for cutting or perforating a web. An exemplary application for laser cutting is in cutting at least a portion of an absorbent article chassis, such as a leg cutout, in a web of interconnected absorbent articles. The laser cutting system provides the ability to modify the leg cutout shape electronically when a manufacturing line changes between absorbent articles of different step sizes, grades, or between different absorbent articles altogether. An exemplary laser that can be used in such cutting can be a $CO_2$ laser, for example, having a wavelength of 980 $cm^{-1}$.

Polyolefin-based films are common to absorbent articles in their use as liquid impermeable barrier, and often need to be cut for a preferred shape in the leg opening of the absorbent article. However, laser cutting the polyolefin based film at high speeds provides difficulties, such that the speed of the machine at such a module may be limited by the ability of the laser assembly to achieve a satisfactory cut. This is especially true for polyethylene films, such as low density polyethylene (LDPE) or linear low density polyethylene (LLDPE).

Accordingly, there is a desire for improved methods and systems for cutting a film, or a web including a film, with laser that allow for increased cutting speeds and improved cut edge characteristics. There is also a desire for a film, or a web including a film, with an improved cut edge.

SUMMARY OF THE DISCLOSURE

In one embodiment, a method of cutting or perforating a web can include providing a web including a film. The film can include a polyolefin polymer and a plurality of particles. The film can include a width and length defining a surface. The method can further include stretching the film to provide a stretched film. Stretching the film can provide a plurality of voids in the stretched film. The method can additionally include providing a laser assembly. The method can include directing a beam of light from the laser assembly upon the surface of the web to cut or perforate the web in at least one location.

In another embodiment, a method of cutting or perforating a web can include providing a web including a film. The film can include a polyolefin polymer and a plurality of particles. The film can include a width in a film cross direction and a length in a film machine direction defining a surface. The method can also include stretching the film in a stretch direction to provide a stretched film. The method can further include providing a laser assembly. The method can additionally include directing a beam of light from the laser assembly upon the surface of the web with relative movement between the beam of light and the web to cut or perforate the web along a path. At least a first portion of the path is substantially parallel to the stretch direction.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
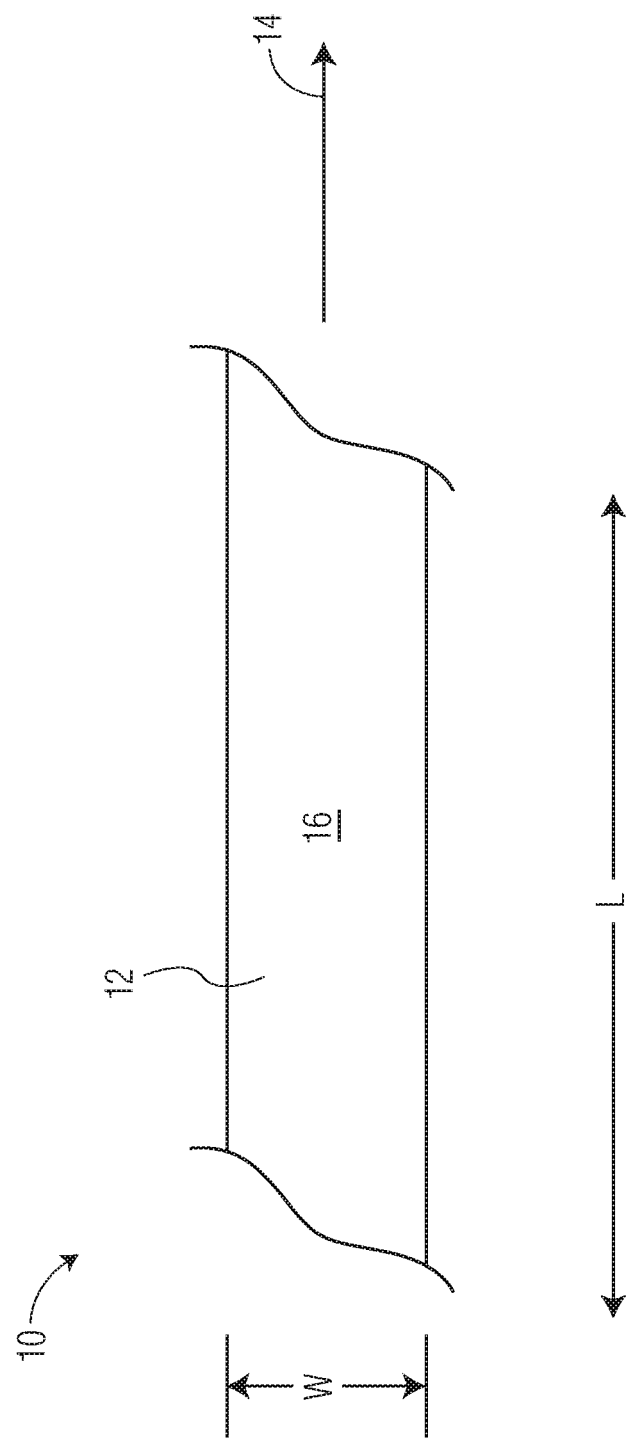
FIG. 1 is a perspective view of a web of film being stretched.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards methods and systems for cutting or perforating a web with a laser, in which the web includes a film that has a plurality of particles and that has been stretched to create a plurality of voids. These methods can increase the laser cutting speed in which the film can be cut or perforated at and can improve the overall cut quality and softness of the cut edge. The present disclosure is also directed to such films, or webs including such a film. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. As used herein, the terminology of "first," "second," "third", etc. does not designate a specified order, but is used as a means to differentiate between different occurrences when referring to various features in the present disclosure. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "polymers" include, but are not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Referring to FIG. 1, a web 10 being stretched is illustrated. The web 10 can be a layer of film 12. The film 12 can be a monolayer of film, or can be a multilayer film. In the context of a multilayer film, the film 12 can include one or more skin layers and one or more tie layers between layers of the film 12. In a multilayer film 12, the various layers can have the same or different components, such as various polyolefin polymers and/or filler particles.

The film 12 can include a polyolefin polymer. For example, the film 12 can be comprised of polyethylene, polypropylene, or combinations thereof. In one embodiment, the film 12 can be comprised of a linear low density polyethylene (LLDPE). As used herein, "linear low density polyethylene" refers to polymers of ethylene and higher alpha olefin comonomers, such as $C_2$-$C_{12}$ comonomers, and combinations thereof, having a density of about 0.900 to 0.935 grams/cm$^3$. In another embodiment, the film 12 can be comprised of a low density polyethylene (LDPE). As used herein, "low density polyethylene" refers to a polyethylene having a density between about 0.91 and 0.925 grams/cm$^3$. It is to be contemplated that a film 12 may have various other polymers and be still be within the scope of this disclosure.

The film 12 can additionally include a plurality of particles. If the film 12 is a multilayer film, particles can be added to one or more layers of the film 12. In some embodiments, the particles can be carbon black, phosphates, phosphites, sulfates, sulfites, carbonates, polyvinyl butyral, mica, kaolinite, alumina, polyethylene terephthalate, and combinations thereof. In some preferred embodiments, the plurality of particles can be $BaSO_4$, $BaPO_4$, $CaCO_3$, $CaSO_4$, and combinations thereof. The particles can be added prior to extrusion of the film 12, using techniques known by one of ordinary skill in the art.

The particles can be provided at various concentrations in the film 12. For example, in some embodiments, the plurality of particles in the film 12 can provide a concentration from about 10% to about 60% in the film 12, or more preferably from about 15% to about 50%, or even more preferably from about 20% to about 40% of the film 12 (by total weight of the film 12).

The film 12 can include a length L and a width W. The film 12 can define a surface 16. The length L of the film 12 can be aligned with the machine direction in which the film 12 is produced. As shown in FIG. 1, the film 12 can be stretched in a stretch direction 14. The stretch direction 14 can be aligned with the machine direction of the film 12. In some embodiments, the film 12 can be stretched in a stretch direction 14 that is perpendicular to the machine direction, or in other words, aligned with the cross direction of the film 12. In some embodiments, the film 12 can be stretched in a stretch direction 14 that is oriented at an angle with respect to the machine direction of the film 12. In some embodiments, the film 12 can be stretched in more than one direction. For example, it is contemplated that the film 12 can be stretched in a first stretch direction that is aligned with the machine direction of the film 12 and be stretched in a second stretch direction that is aligned with the cross direction of the film 12. In some embodiments, the film 12 can be stretched at a percent stretch of between about 150% to about 600%, and more preferably from about 200% to about 500%, and even more preferably from about 250% to about 500%.

In stretching the film 12 a plurality of voids can be provided in the film 12, as will be discussed and shown in further detail below. The plurality of voids can provide a void volume percentage for the film, the methodology for calculating being described further below in relation to various SEM images. In some embodiments, the void volume percentage for the film 12 can be between about 1% to about 25%, and in some embodiments from about 1.5% to about 20%, and in some embodiments from about 2% to about 15%. After stretching the film 12, the film 12 can be relaxed. In some situations, the film 12 can then be spooled in a converting operation for use at another location. In other situations, the film 12 can be stretched and transferred directly to a machine line for further processing. In some embodiments, the film 12 can be stretched prior to being cut, as described further herein. However, it is contemplated that the film 12 could be stretched while being cut in some embodiments.

Depending on the various particles in the film and the stretching employed, the voids can be of various average size, the methodology for calculating the average size of a void being described further below. As will discussed further below, the voids can have an average size from about 0.24 µm to about 2.00 µm, or from about 0.30 µm to about 2.00 µm.

Figure 2:
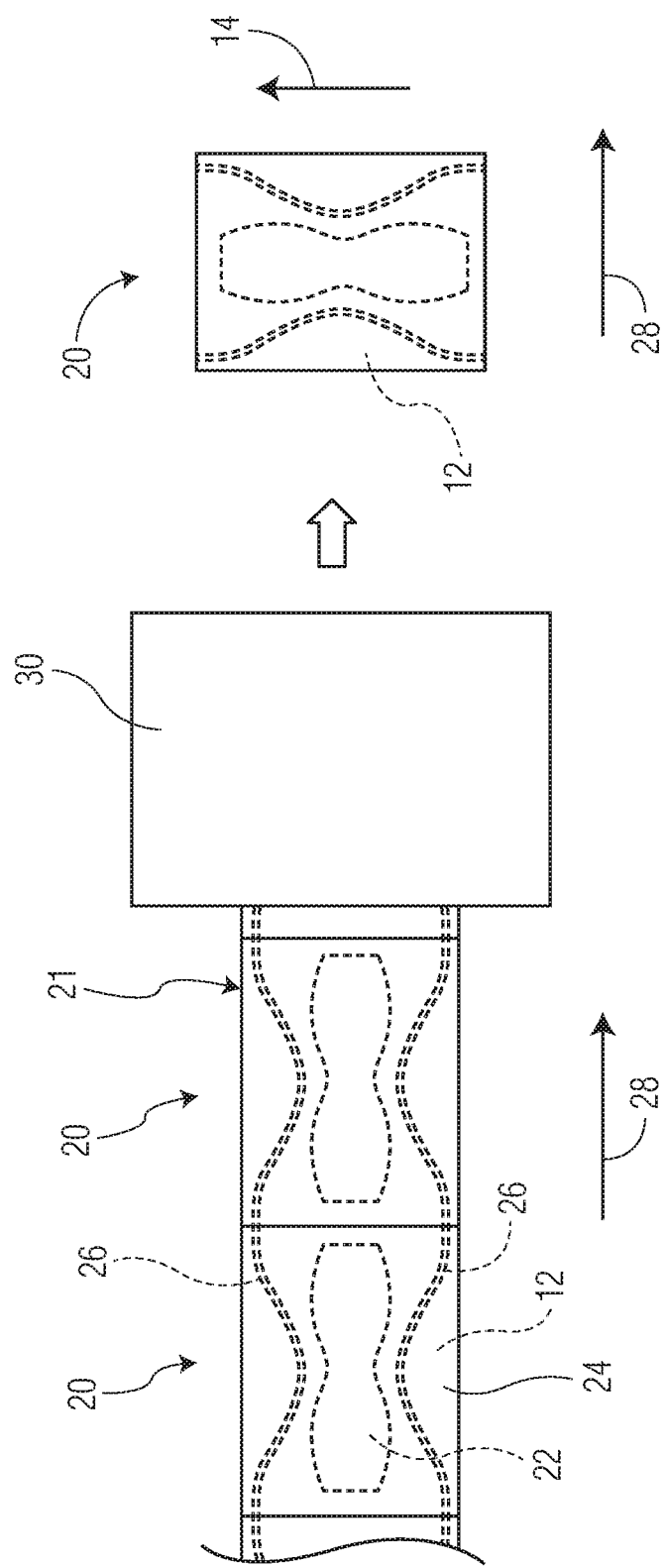
FIG. 2 is a top view of a web of interconnected absorbent assemblies, including the film of FIG. 1, and depicts an exemplary absorbent assembly being cut from the web and rotated.

In some embodiments, the film 12 can be used to form at least a portion of an absorbent article, however, it is to be appreciated that the films 12 described herein can be utilized as a film independent of any other feature, or can be combined in various other configurations, webs, and/or products without departing from the scope of this disclosure. In one embodiment where the film 12 forms at least a portion of an absorbent article, the film 12 can form at least a portion of an absorbent assembly 20. In FIG. 2, a series of interconnected absorbent assemblies 20 are shown being transferred in the form of a web 21. An absorbent assembly 20 can include components, including, but not limited to, the film 12, an absorbent body 22 including cellulosic fibers and/or superabsorbent material, one or more non-woven layers 24, and elastic material 26. In some embodiments, the film 12 can form at least a portion of an outer cover for an absorbent article. In some embodiments, a non-woven layer 24 can form a bodyside liner for an absorbent article. If included in the absorbent assembly 20, the elastic material 26 can be in various forms, such as elastic strands as depicted. The elastic strands can help form a leg gasket on an absorbent article and provide enhanced fit. It is to be contemplated that the absorbent assemblies 20 depicted and described herein are merely exemplary, and could be provided in a variety of configurations without departing from the scope of this disclosure.

As also depicted in FIG. 2, the web 21 of absorbent assemblies 20 can be initially transferred in a direction 28 that is parallel to the stretch direction 14 of the film 12, as previously depicted in FIG. 1. In some embodiments, the web 21 of absorbent assemblies 20 can be transferred utilizing known conveying equipment (not shown for clarity) to a rotating module 30 that can cut individual absorbent assemblies 20 from the web 21 and rotate the individual absorbent assemblies 20. The general construction and operation of such a rotating module 30 is well known and is exemplified by U.S. Pat. Nos. 5,716,478 and 5,759,340 issued to Boothe et al. and U.S. Pat. No. 6,139,004 issued to Couillard et al., each of which is incorporated herein by reference in its entirety to the extent not inconsistent herewith. After such rotation, absorbent assembly 20 can be oriented such that the stretch direction 14 in the film layer 12 is no longer aligned with the direction 28 of transferring the absorbent assembly 20. In some embodiments, as depicted in FIG. 2, the film layer 12 of the absorbent assembly 20 can be oriented such that the stretch direction 14 in the film layer 12 is perpendicular to the direction 28 of transferring the absorbent assembly 20.

Figure 3:
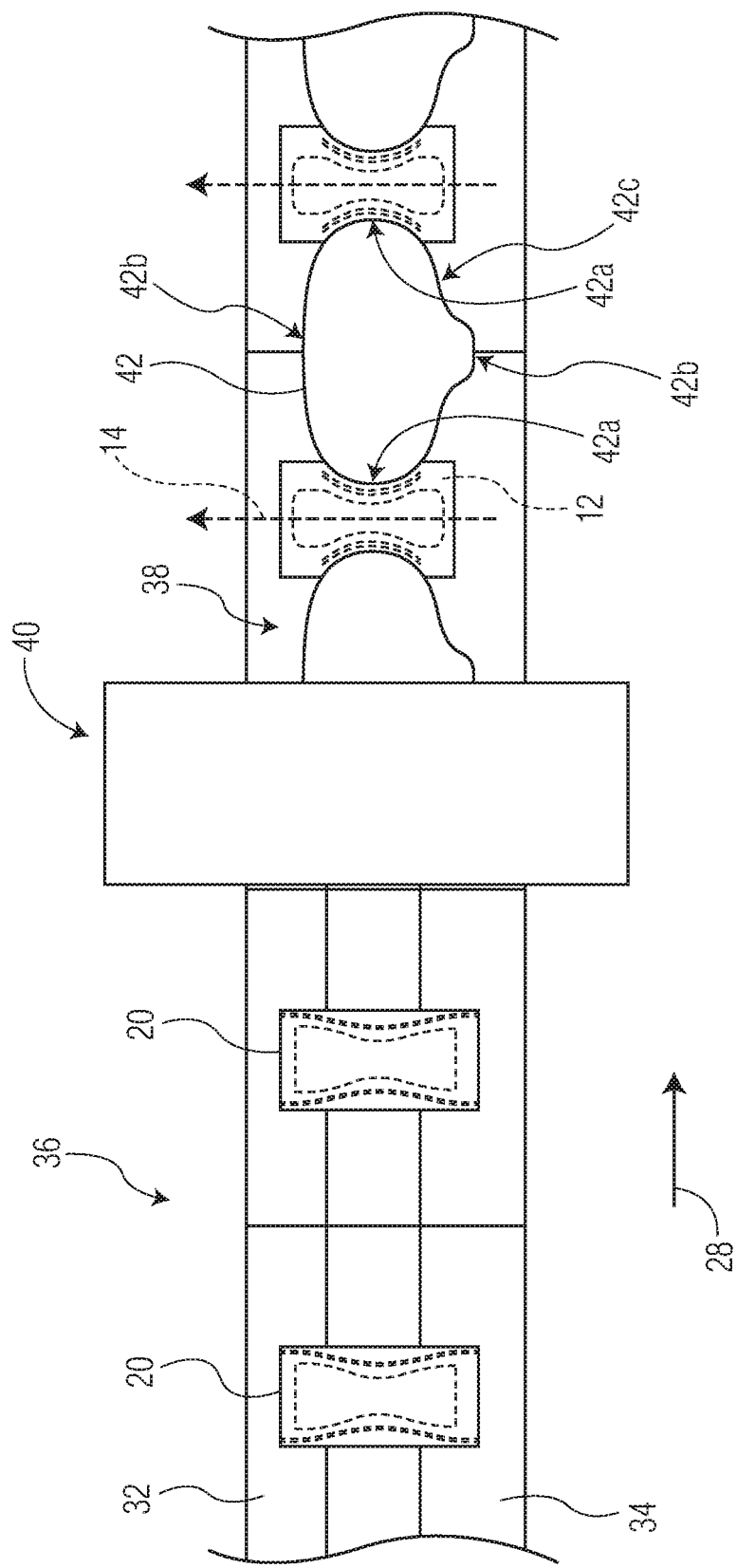
FIG. 3 is a top view of an exemplary web of interconnected absorbent articles, each including an absorbent assembly such as depicted in FIG. 2, and depicts an exemplary leg cutout path completed by a laser assembly.

Turning to FIG. 3, in some embodiments the absorbent assembly 20 can be coupled to one or more webs after being cut and rotated by the rotating module 30. In some embodiments, the absorbent assembly 20 can be coupled to a web 32 providing front waist panel material for an absorbent article and the absorbent assembly 20 can be coupled to a web 34 providing rear waist panel for an absorbent article, each web 32, 34 including materials known to one of ordinary skill in the art such as nonwoven materials and elastic materials. In some embodiments, the absorbent assembly 20 can be coupled to such webs 32, 34 by the rotating module 30 after being cut and rotated. Coupling can occurring through adhesives and/or other techniques such as pressure bonding, ultrasonic bonding, heat welding, or other suitable techniques. Once the absorbent assembly 20 is coupled to the webs 32, 34 providing front and rear waist panel material, respectively, the overall assembly provides a continuous web 36 of absorbent articles.

The web 36 of absorbent articles can then be transferred to a laser assembly 40 by transferring the web 36 in a direction 28. Alternatively, the laser assembly 40 could be moved with respect to the web 36 as well. In either case, the laser assembly can direct a beam of light from the laser assembly upon the surface of the web 36 to either cut or perforate the web 36 in at least one location by having relative movement between the beam of light and the web 36 to cut or perforate the web 36 in at least one location. As depicted in FIG. 3, the laser assembly 40 can direct the laser(s) to a surface of the web 36, such as the top surface 38 of the web 36 to cut or perforate the web 36 in at least one location. In the preferred embodiment shown in FIG. 3, the web 36 of absorbent articles is cut in a generally oval-shaped path 42 that provides leg cutouts on adjacent absorbent articles. Of course, this specific shape of the path 42 can be modified for various different absorbent articles or other products in which the methodology may be utilized without departing from the scope of this disclosure. The path 42 provided by the cut in the web 36 of absorbent articles can cut absorbent assembly 20 including the film 12. In some embodiments, such as depicted in FIG. 3, the path 42 can cut the web 32 providing the front panel material and/or the web 34 providing the rear panel material.

In some embodiments, at least a first portion 42a of the path 42 in which the laser cuts or perforates the web 36 is substantially parallel to the stretch direction 14 of the film layer 12. The first portion 42a of the path 42 in which the laser cuts or perforates the web 36 that is substantially parallel to the stretch direction 14 of the film layer 12 can be viewed near the left and right sides of the path 42 as depicted in FIG. 3. In some embodiments, another portion 42b of the path 42 in which the laser cuts or perforates the web 36 can be substantially perpendicular to the stretch direction 14 of the film layer 12. For example, this portion 42b of the path 42 that is substantially perpendicular to the stretch direction 14 can be viewed near the top and bottom of the path 42 as shown in FIG. 3. Other portions, such as portion 42c, of the path 42 can be neither parallel nor perpendicular to the stretch direction 14 of the film layer 12. Thus, one benefit to the method as described herein is the ability to cut the film layer 12 in various directions with respect to the stretch direction 14 of the film layer 12, including cutting in a direction parallel to the stretch direction 14 of the film layer 12.

One exemplary embodiment of a laser assembly 40 can be a Rofin OEM-65iX 10.25 μm 650 W $CO_2$ laser assembly having a focused spot size of about 210 μm in diameter (manufactured by Rofin-Sinar UK Ltd.). For experimental cutting described herein, the laser assembly 40 was set to a power of 110 W, with a pulse frequency of about 30 Khz. In some embodiments, the laser assembly 40 may have two or more lasers. However, it can be appreciated that the laser(s) from the laser assembly 40 can be operated at various wavelengths, ranging from about 9.4 μm to about 10.6 μm, or more preferably from 10.0 μm to about 10.3 μm, or even more preferably from about 10.2 μm to about 10.3 μm. The laser(s) from the laser assembly 40 can be operated at various power settings, ranging from about 65 W to about 1200 W, or more preferably from about 100 W to about 1000 W.

For purposes of testing, various film layers 12 (experimental Codes 1-7) were created with different particles and stretch rates as described in Table 1 and compared against control codes 8 and 9 that included. All the cutting was completed using the laser assembly described above, with a duty cycle of 9.5%. The thickness measurement was taken as gauge thickness, not measured from any SEM images that were later produced. The maximum process cut speed listed in Table 1 was the maximum speed that was achieved that was able to provide a clean cut in the respective exemplary film layer 12.

TABLE 1

Code Listing for Experimental Films

| Code No. | Material | Stretch Ratio | Maximum Process Cut Speed (in/sec) | Thickness (mils) |
|---|---|---|---|---|
| 1 | 60% LLDPE, 40% $CaSO_4$ | 300% | 300 | 1.25 |
| 2 | 60% LLDPE, 40% $CaSO_4$ | 0% | 175 | 0.65 |
| 3 | 49% LLDPE, 50% $CaCO_3$, 1% A-3000 (PTFE additive) | 450% | 325 | 0.55 |
| 4 | 50% LLDPE, 50% $CaCO_3$ | 450% | 300 | 0.60 |
| 5 | 50% LLDPE, 50% $CaCO_3$ | 0% | 125 | 0.75 |
| 6 | 60% LLDPE, 40% $BaSO_4$ | 400% | 275 | 0.80 |
| 7 | 60% LLDPE, 40% $BaSO_4$ | 0% | 350 | 0.50 |
| 8 | 100% LLDPE | 400% | 50 | 0.91 |
| 9 | 100% LLDPE | 0% | 25 | 0.75 |

As demonstrated in Table 1, experimental film layers 12 including particles provided a benefit in increased maximum cutting speeds in codes 1-7 in comparison to the control codes 8 and 9 that included 100% LLDPE. Comparing experimental film layers 12 with particles that were stretched in comparison to experimental film layers 12 with particles that were not stretched also showed an increase in maximum cutting speed. For example, the stretched film 12 with calcium sulfate ($CaSO_4$) (Code No. 1) showed significant increase in cutting speed over the non-stretched film 12 with calcium sulfate ($CaSO_4$) (Code No. 2), having respective speeds of 300 in/sec and 175 in/sec. The stretched film 12 with calcium carbonate ($CaCO_3$) (Code Nos. 3 and 4) demonstrated an even larger difference between cut speed compared to non-stretched film 12 with calcium carbonate ($CaCO_3$) (Code No. 5), with respective cut speeds of stretched film 12 at 325 in/sec (Code No. 3) and 300 in/sec (Code No. 4), compared to the cut speed of 125 in/sec for the non-stretched film 12 (Code No. 5). However, the stretched film 12 including barium sulfate ($BaSO_4$) (Code No. 6) did not provide an increased cutting speed in comparison to the non-stretched film including barium sulfate ($BaSO_4$) (Code No. 6), as the stretched film 12 had a cut speed of 275 in/sec (Code No. 6) and the non-stretched film 12 had a cut speed of 350 in/sec.

Figure 4A:
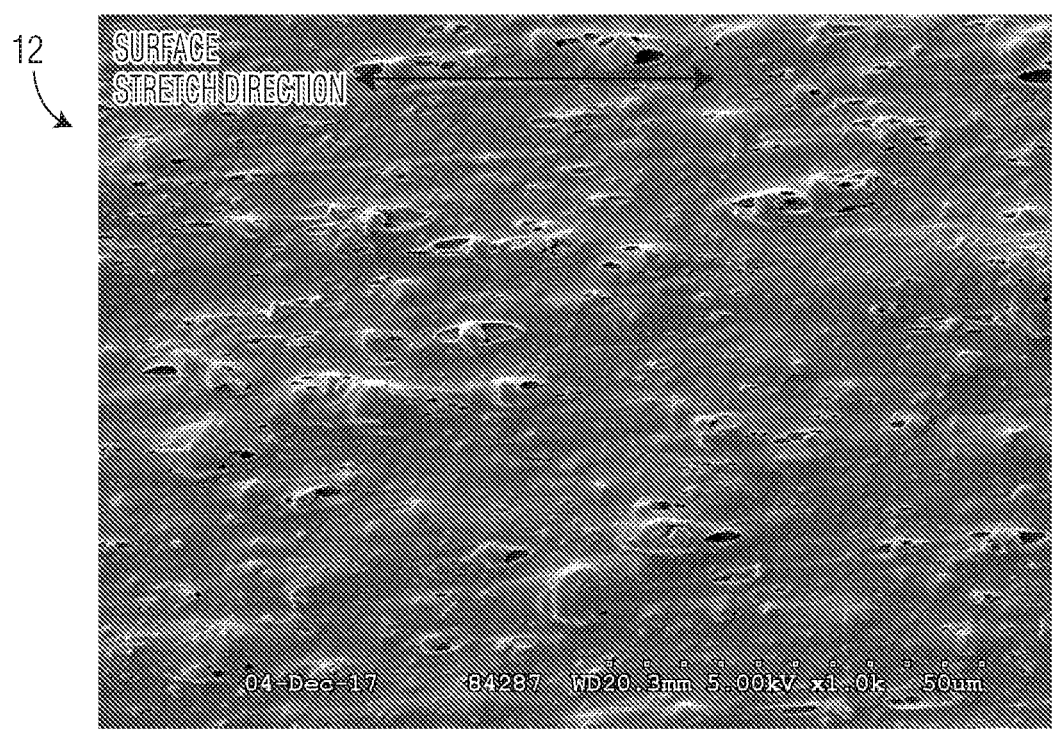
FIG. 4A is a scanning electron microscope (SEM) image of a surface of an exemplary film including 50% $CaCO_3$ after stretching at a stretch rate of 450%.
Figure 4B:
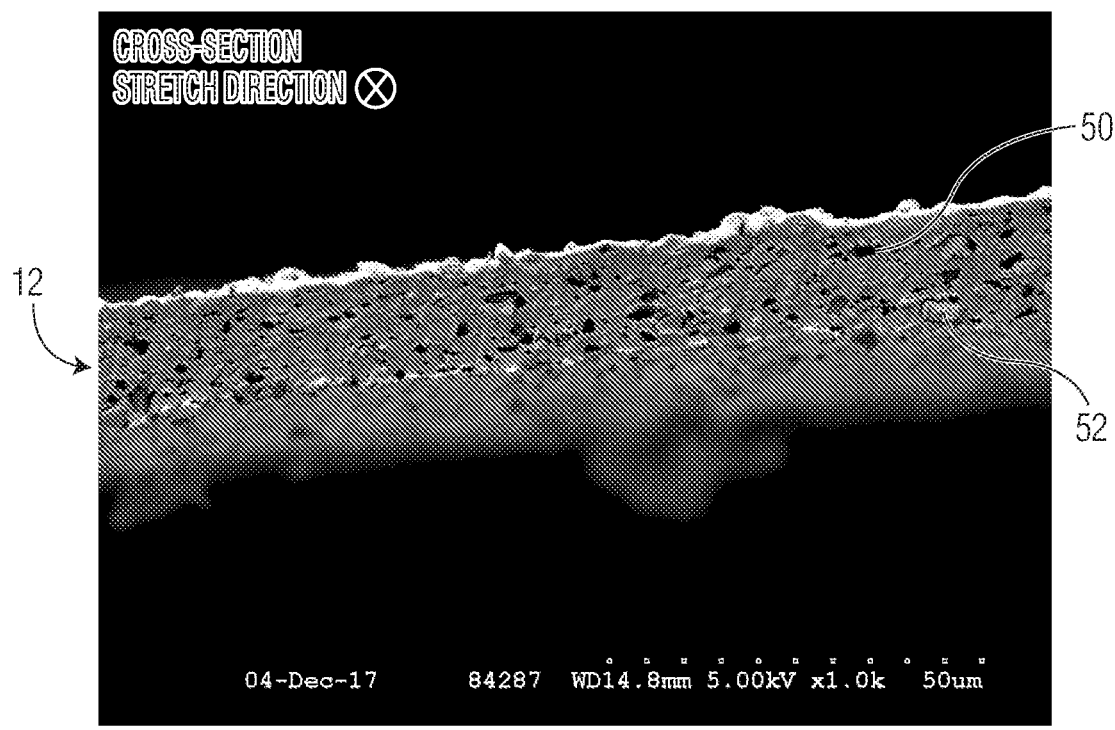
FIG. 4B is an SEM image of a cross-section of the film of FIG. 4A.
Figure 5A:
FIG. 5A is an SEM image of a surface of an exemplary film including 50% $CaCO_3$ after stretching at a stretch rate of 450%.
Figure 5B:
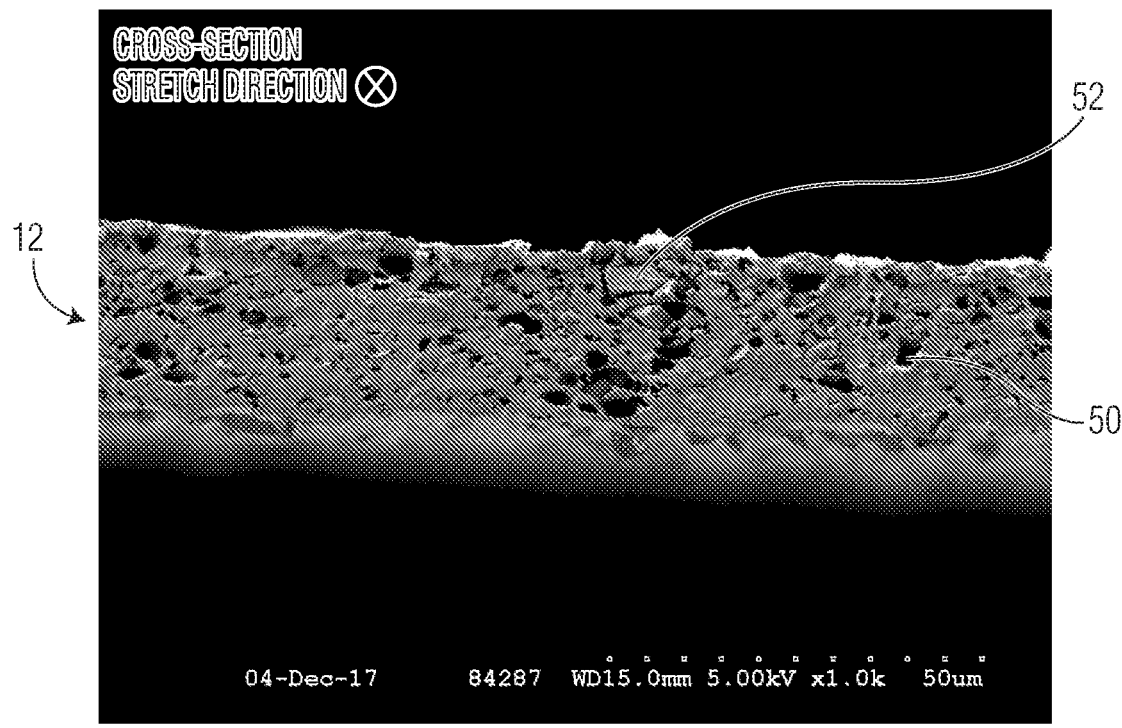
FIG. 5B is an SEM image of a cross-section of the film of FIG. 5A.
Figure 6A:
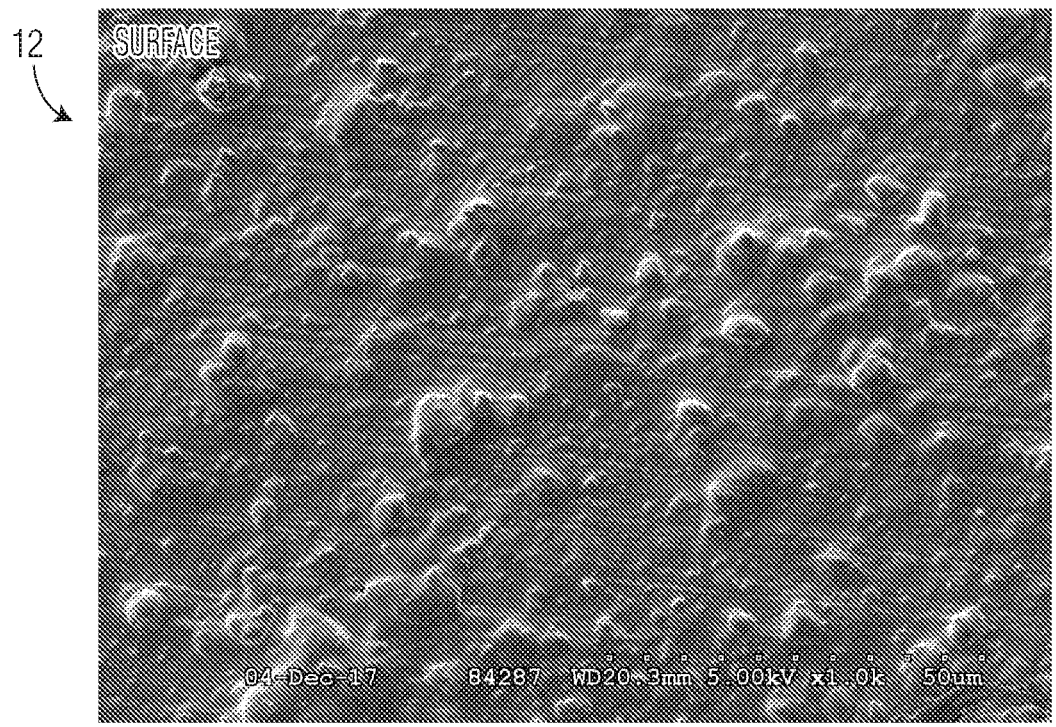
FIG. 6A is an SEM image of a surface of an exemplary film including 50% $CaCO_3$ with no stretching.
Figure 6B:
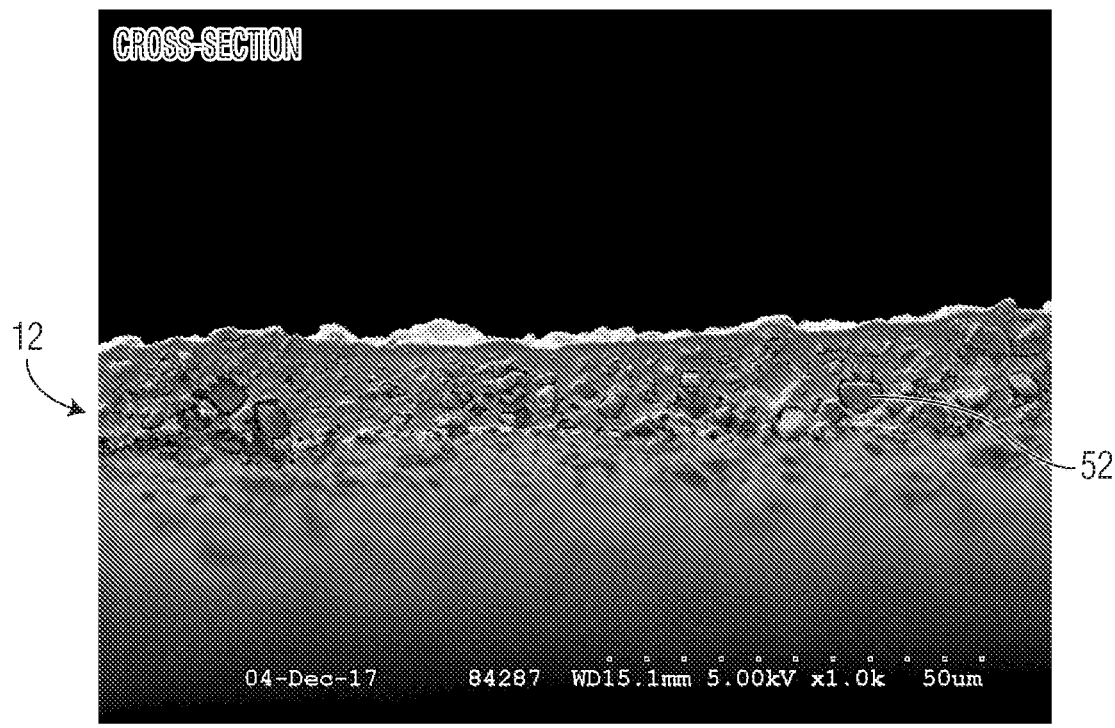
FIG. 6B is an SEM image of a cross-section of the film of FIG. 6A.

Various scanning electron microscope (SEM) images were taken of experimental film layers 12 for Code Nos. 1-7 described above and listed in Table 1. For example, FIG. 4A illustrates an SEM image of an exemplary film 12 of Code No. 3, and FIG. 4B provides an illustration of a cross-section of an exemplary film 12 of Code No. 3. FIGS. 5A and 5B show similar respective views for an exemplary film 12 of Code No. 4. Similarly, FIGS. 6A and 6B illustrate a surface and cross-section view, respectively, for an exemplary film of Code No. 5. Code Nos. 3 and 4, which are stretched films 12 including particles 52 of $CaCO_3$ provided a plurality of voids 50 (only one void 50 and one particle 52 being labeled for clarity of SEM images) that were created due to the solid-state stretching of the films 12, which were particularly evident in the cross-sectional views depicted in FIGS. 4B and 5B. On the other hand, the non-stretched film 12 including particles 52 of $CaCO_3$ did not provide a plurality of voids 50, as shown in FIGS. 6A and 6B.

Laser absorption on the infrared (IR) spectra was also tested on the experimental films 12 for Code Nos. 3-5, as it was believed that an increase in the absorption levels of IR spectra may be leading to the increased cutting speeds of the stretched films 12 of Code Nos. 3 and 4 that included the particles of $CaCO_3$. IR spectra were acquired using a Spectra Tech Golden Gate Single bounce ATR accessory equipped with a diamond cell ATR crystal on a Nicolet Nexus 670 FTIR, averaging 32 scans per sample at 4 $cm^{-1}$ resolution. Specific IR Experimental Conditions included Data Collection Information of: number of scans: 32; collection length 38.5 sec; resolution: 4.000; levels of zero filling: 0; number of scan points: 8480; number of FFT points: 8192; laser frequency: 15798.3 $cm^{-1}$; interferogram peak position: 4096; apodization: Happ-Genzel; phase correction: Mertz; number of background scans: 64; background gain: 8.0. The spectrometer information included: spectrometer: Nexus 670; source: IR; detector: DTGS KBr; smart accessory ID: unknown; beamsplitter: KBr; sample spacing: 2.0000; digitizer bits: 20; optical velocity: 0.6329; aperture: 100.00; sample gain: 8.0; high pass filter: 200.0000; low pass filter: 11000.0000.

Figure 7:
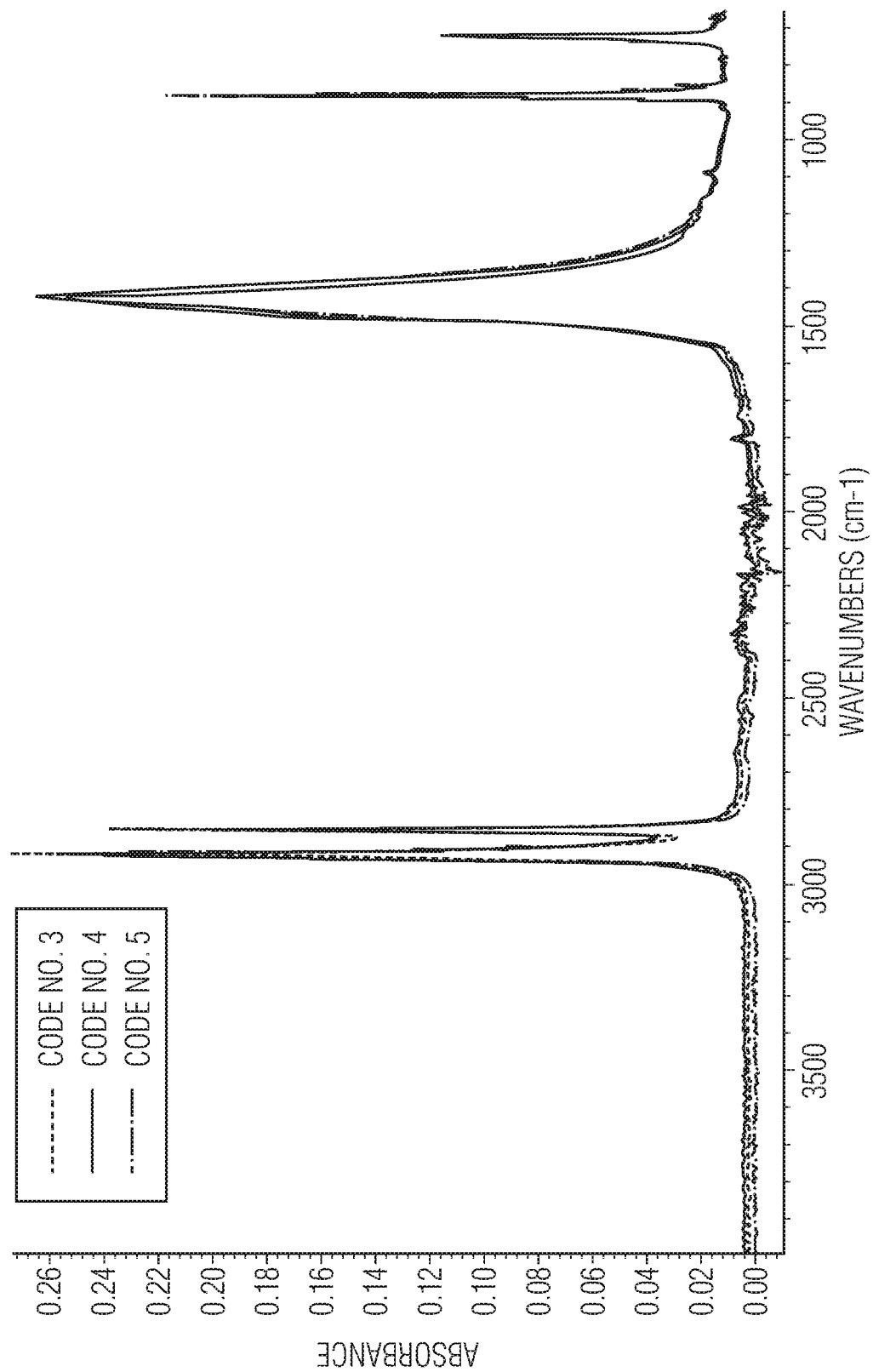
FIG. 7 is a graph depicting the infrared (IR) spectra absorbance for the stretched films depicted in FIGS. 4A-5B and the unstretched film depicted in FIGS. 6A and 6B.
Figure 8A:
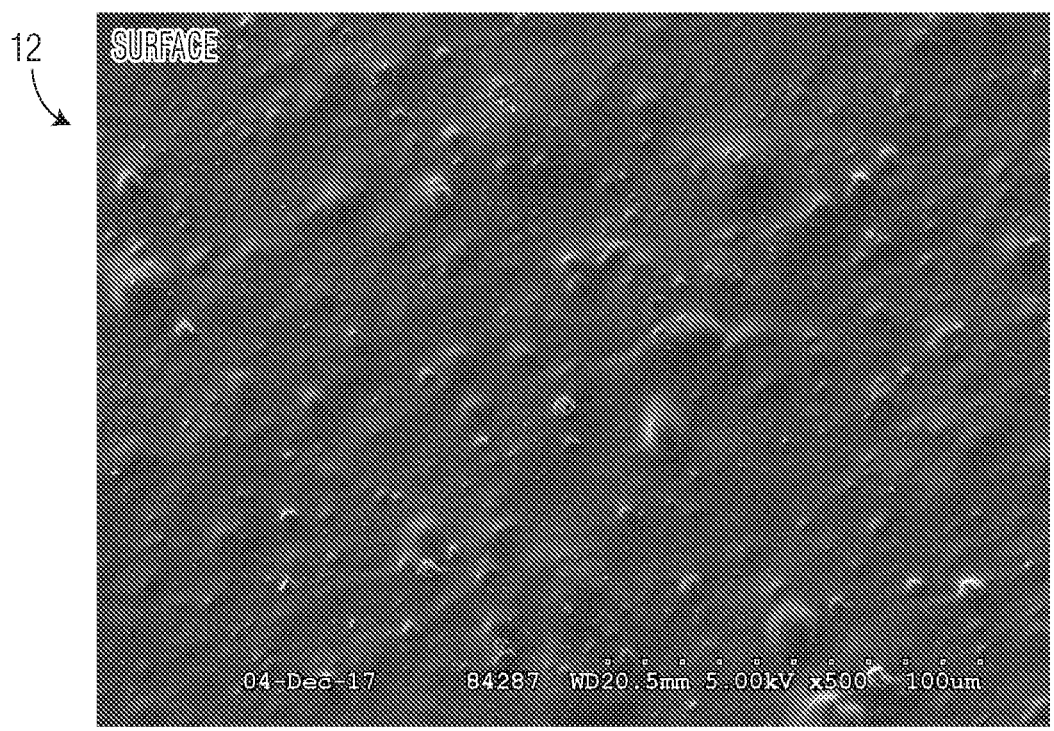
FIG. 8A is an SEM image of a surface of an exemplary film including 40% $CaSO_4$ with no stretching.
Figure 8B:
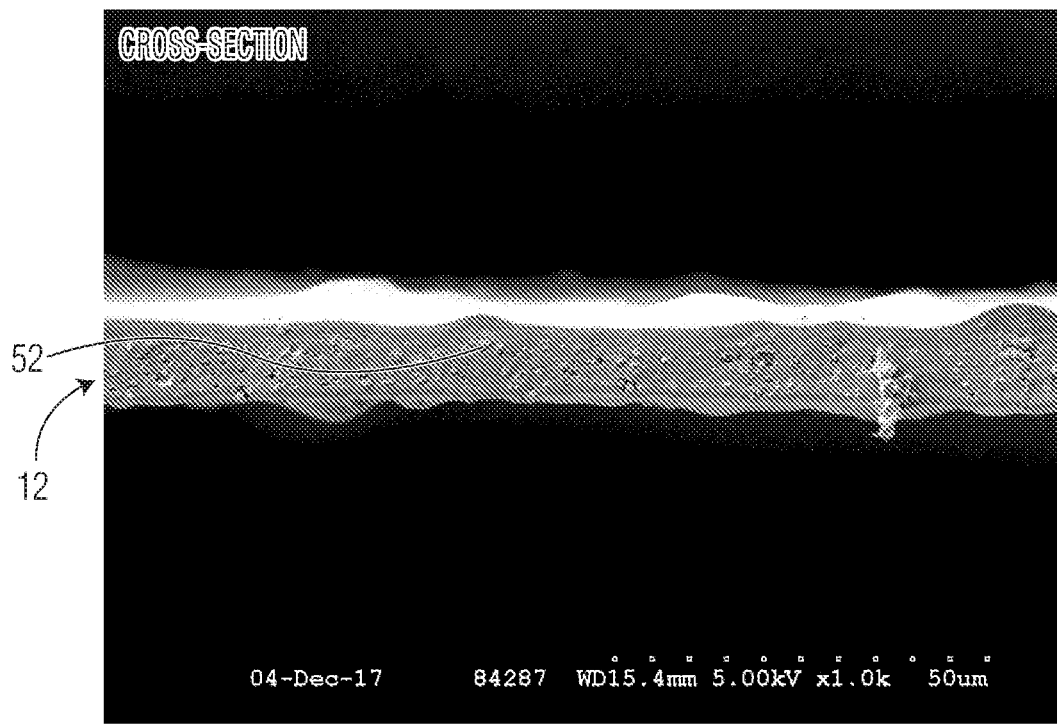
FIG. 8B is an SEM image of a cross-section of the film of FIG. 8A.
Figure 9A:
FIG. 9A is an SEM image a surface of an exemplary film including 40% $CaSO_4$ after stretching at a stretch rate of 300%.
Figure 9B:
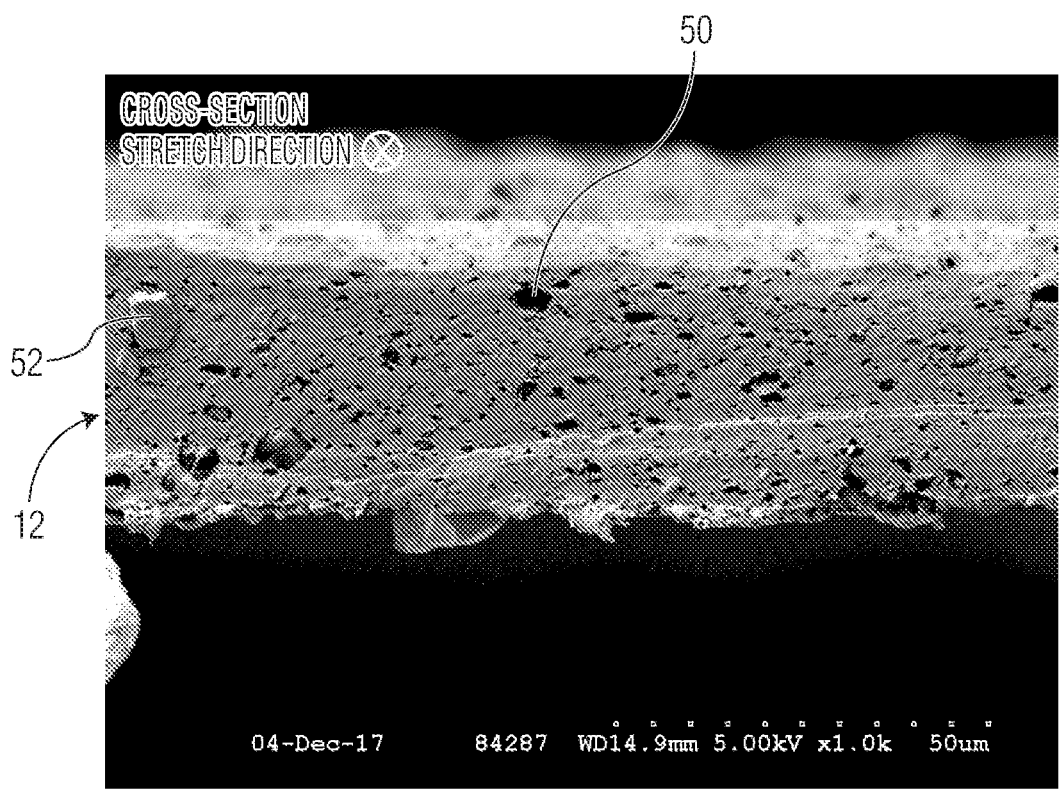
FIG. 9B is an SEM image of a cross-section of the film of FIG. 9A.

Despite the initial belief that an increase in the absorption levels of IR spectra may be leading to the increased cutting speeds of the stretched films, FIG. 7 illustrates the IR spectra absorbance for Code Nos. 3-5, and no difference was detected for IR spectra absorbance between the stretched films 12 (Code Nos. 3 and 4) as compared to the non-stretched film 12 (Code No. 5). Although not to be bound by theory, but it is believed that the increase in laser cutting speed that was obtainable through the films 12 of codes including particles 52 of $CaCO_3$ may be due to the micro voids 50 that may amplify the laser scattering in the voids 50 resulting in increased heat generation to promote cutting.

FIGS. 8A-9B depict SEM images and cross-sections for Code Nos. 1 and 2 that include particles of $CaSO_4$. Similar to the results for the films 12 including $CaCO_3$ particles 52 in Code Nos. 3-5 and the images depicted in FIGS. 4A-6B, the non-stretched film 12 including $CaSO_4$ particles 52 (Code No. 1) depicted in FIGS. 8A and 8B did not include voids 50, but the stretched film 12 including $CaSO_4$ particles 52 (Code No. 2) depicted in FIGS. 9A and 9B did include a plurality of voids 50. Referring back to Table 1 shows that the stretched film 12 including $CaSO_4$ particles 52 (Code No. 2) exhibited higher cutting speeds.

Figure 10:
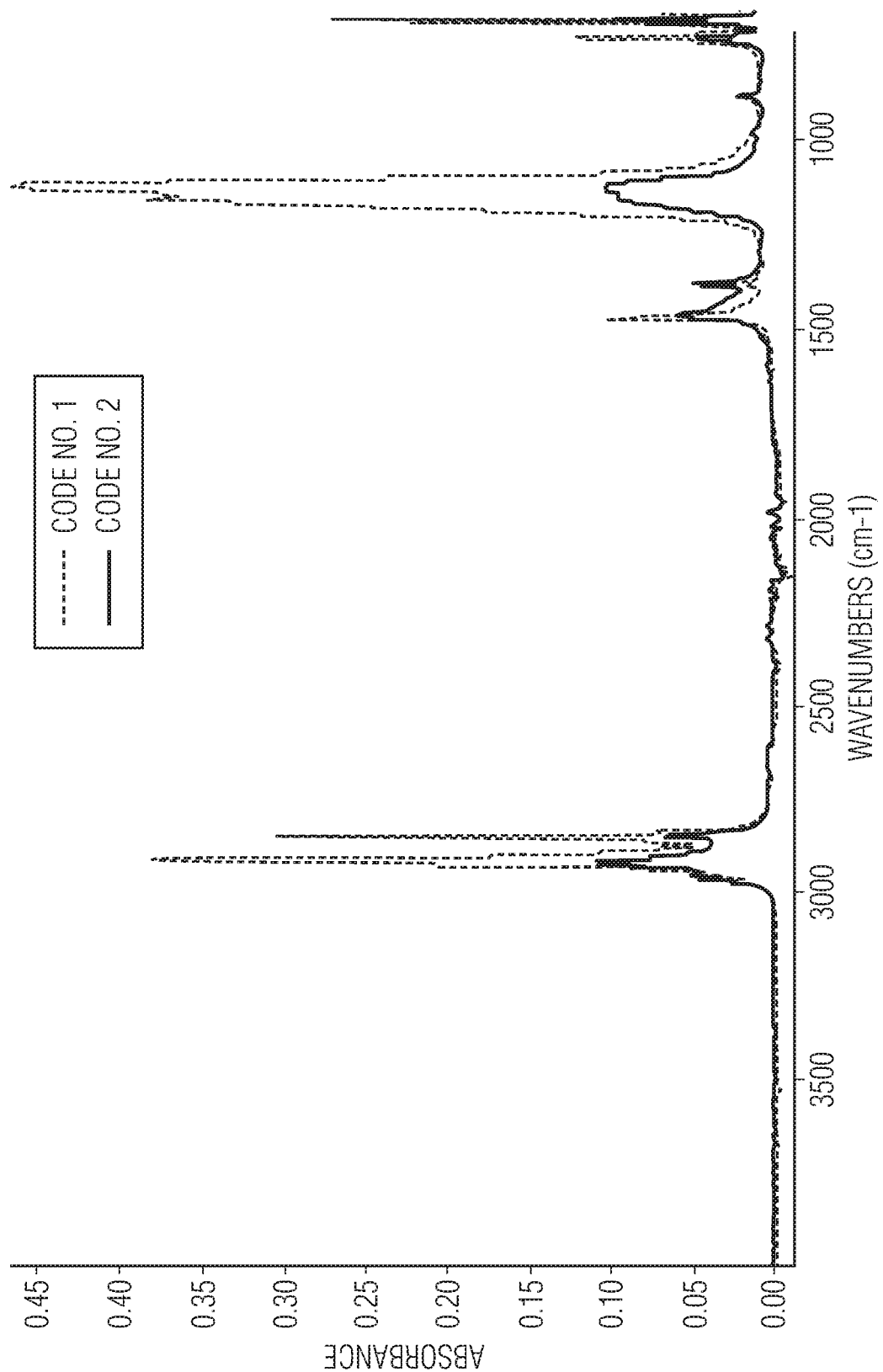
FIG. 10 is a graph depicting the IR spectra absorbance for the stretched film depicted in FIGS. 9A and 9B and the unstretched film depicted in FIGS. 8A and 8B.

The IR spectra absorbance was also measured for the films 12 of Code Nos. 1 and 2 and is shown in FIG. 10. FIG. 10 illustrates that the IR spectra absorbance is rather similar between the films 12 of Code Nos. 1 and 2, especially at the wavelength of 980 $cm^{-1}$. Similar to the discussion above with respect to the particles 52 of $CaCO_3$ for films 12 in Code Nos. 3-5 and the IR spectra absorbance depicted in FIG. 7, this result further supports that the voids 50 created in the film 12 of Code No. 1 including $CaSO_4$ particles 52 due to stretching the film 12 are leading to the increased cutting speed exhibited for Code No. 1 in comparison to Code No. 2, which included $CaSO_4$ particles 52, but was not stretched, and thus, did not have voids 50.

FIG. 10 does demonstrate some differences in the IR spectra absorbance for Code Nos. 1 and 2. Specifically, it is believed the stretched film 12 including $CaSO_4$ particles 52 (Code No. 2) caused the polyethylene bands to increase in intensity by creating an oriented film 12, which is shown in a shift in the band at 1471 $cm^{-1}$ band and a peak at 1130 $cm^{-1}$. IR spectra are sensitive to the conformation and packing of the chain molecules. As the film 12 is stretched, the polymer chains align and become more ordered, going from a more amorphous state to a more crystalline state. In the IR region, it is known that as the sample becomes more ordered it affects the shape, position, and intensities of the absorption bands. The magnitude of the changes can be dependent upon the change in the physical state of the system.

Figure 11A:
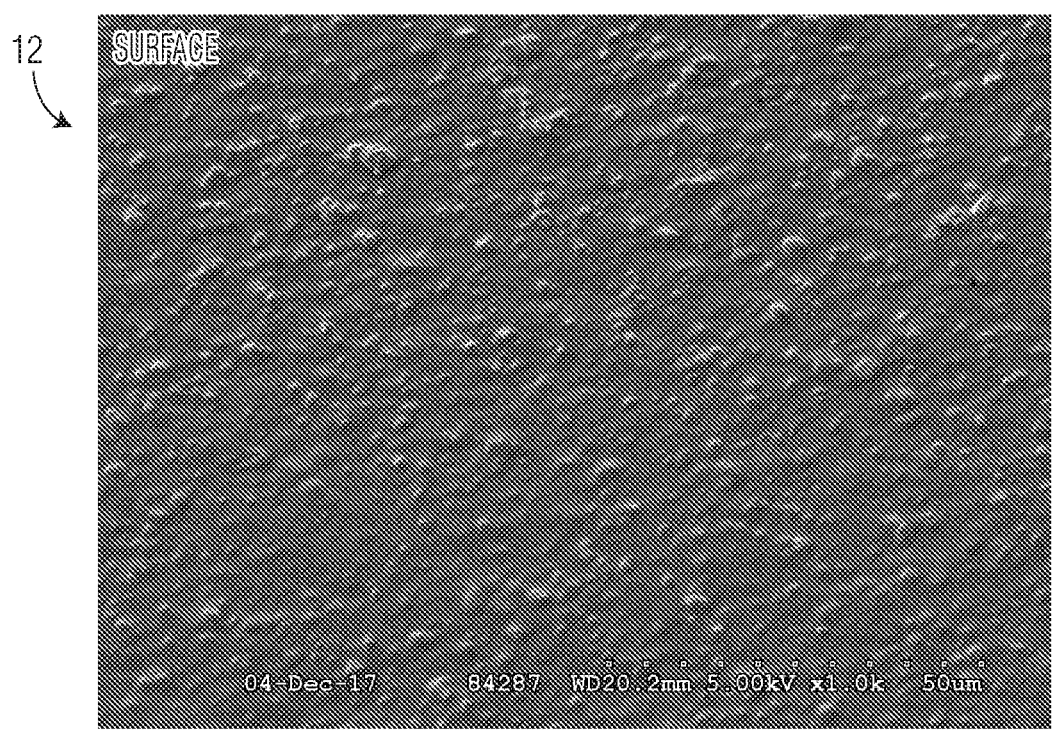
FIG. 11A is an SEM image of a surface of an exemplary film including 40% $BaSO_4$ with no stretching.
Figure 11B:
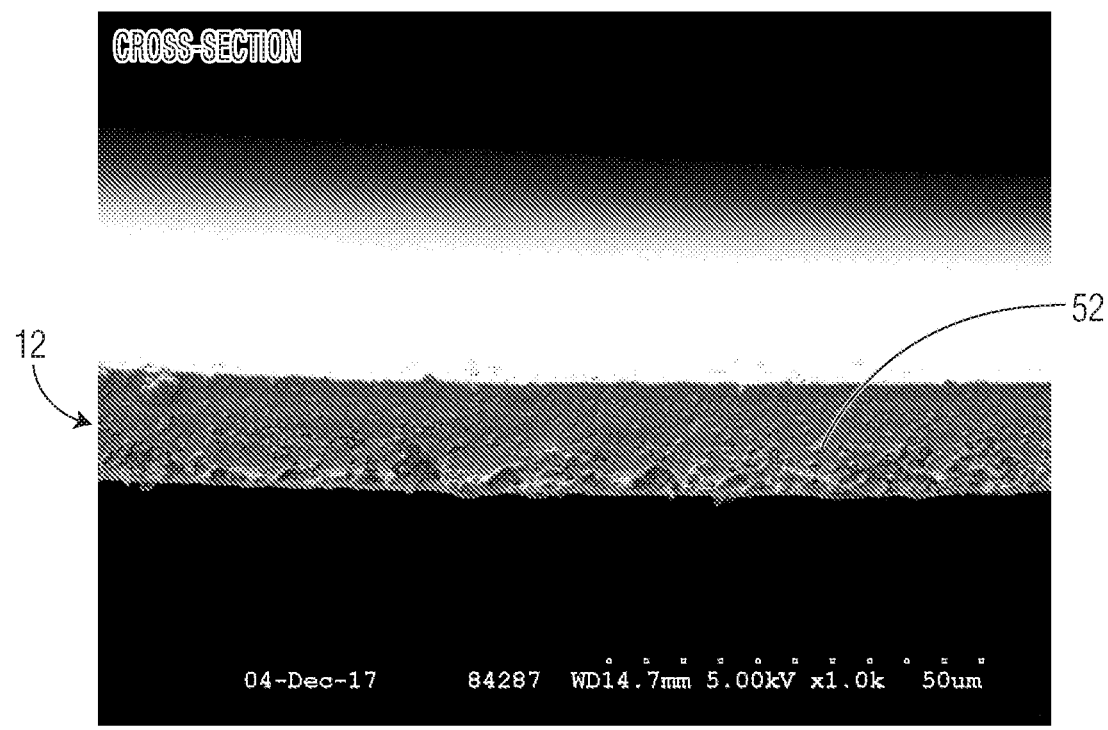
FIG. 11B is an SEM image of a cross-section of the film of FIG. 11A.
Figure 12A:
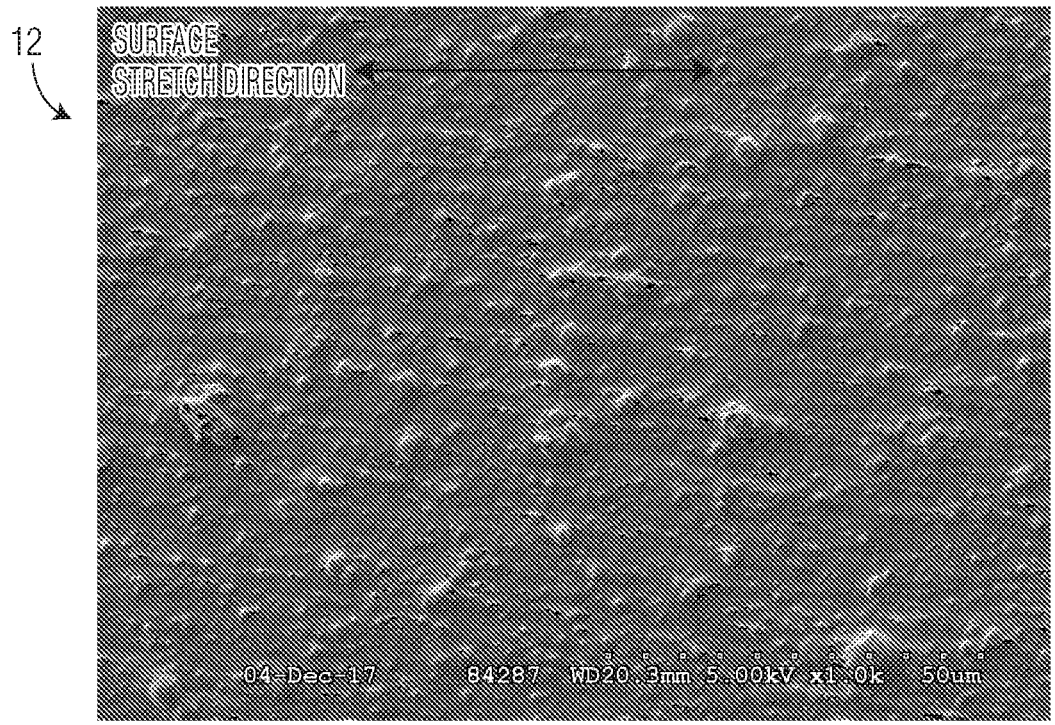
FIG. 12A is an SEM image a surface of an exemplary film including 40% $BaSO_4$ after stretching at a stretch rate of 400%.
Figure 12B:
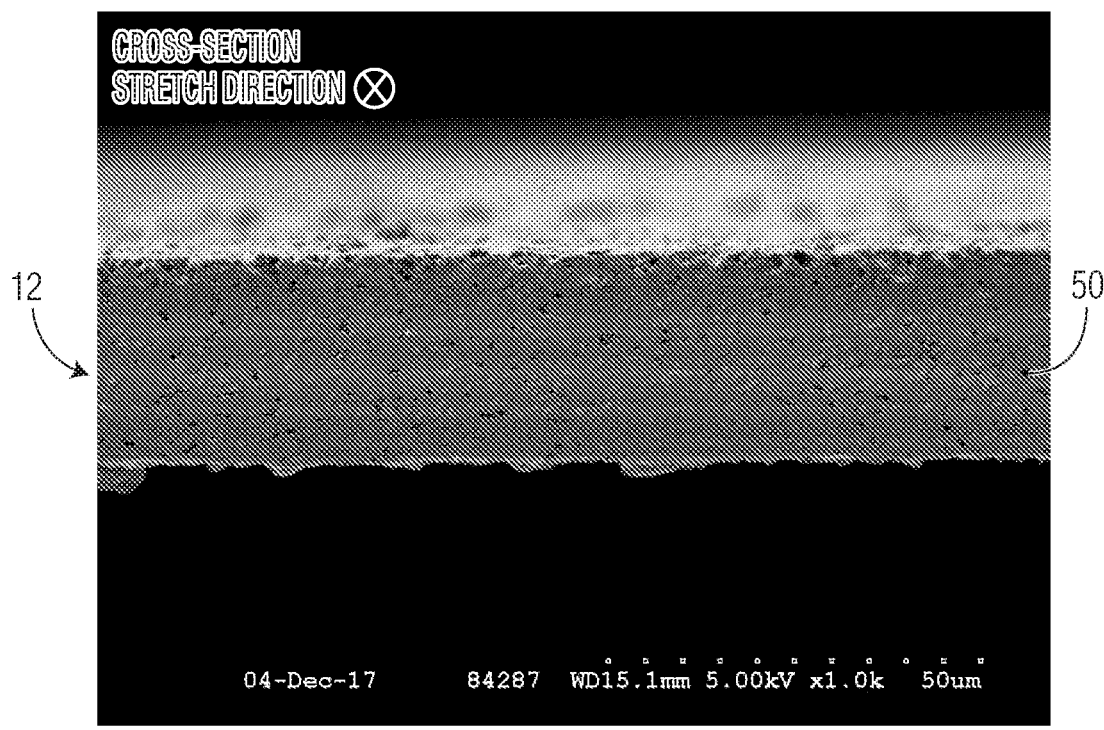
FIG. 12B is an SEM image of a cross-section of the film of FIG. 12A.

SEM images and IR absorbance was also completed for Code Nos. 6 and 7 for films 12 that included BaSO₄ particles 52. FIGS. 11A and 11B depict SEM images for the non-stretched film 12 including BaSO₄ particles 52 (Code No. 7) and FIGS. 12A and 12B depict SEM images for the stretched film 12 including BaSO₄ particles 52 (Code No. 6). Similar to other non-stretched films 12 described and illustrated above in SEM images, the non-stretched film 12 including BaSO₄ particles 52 (Code No. 7) did not include voids 50. Reviewing FIGS. 12A and 12B depicting the stretched film 12 including BaSO₄ particles 52 (Code No. 6) exhibited that the stretched film 12 did not include voids 50, but they appeared to be of significantly smaller size (see FIG. 12B). Referring back to Table 1 shows that the stretched film 12 including BaSO₄ particles 52 (Code No. 6) did not have any improvement in cut speed as compared to the non-stretched film 12 including BaSO₄ particles 52 (Code No. 7). In fact, the non-stretched film 12 (Code No. 7) had an increased cut speed compared to the stretched film 12 (350 in/sec as compared to 275 in/sec). The increase in cut speed for the non-stretched film 12 including BaSO₄ particles 52 (Code No. 7) in comparison to the stretched film 12 including BaSO₄ particles 52 (Code No. 6) was believed to be due to the reduced thickness of the non-stretched film 12 (Code No. 7). It is believed that the higher density of the BaSO₄ particles 52 of 4.49 g/cc as compared to the density of the CaCO₃ particles 52 of 2.71 g/cc and the density of CaSO₄ particles 52 of 2.96 g/cc led to a smaller void size. The smaller void size is believed to provide a much weaker laser scattering, and thus, a less significant difference in laser cutting speed through stretching as compared to films including particles 52 of CaCO₃ or CaSO₄.

Figure 13:
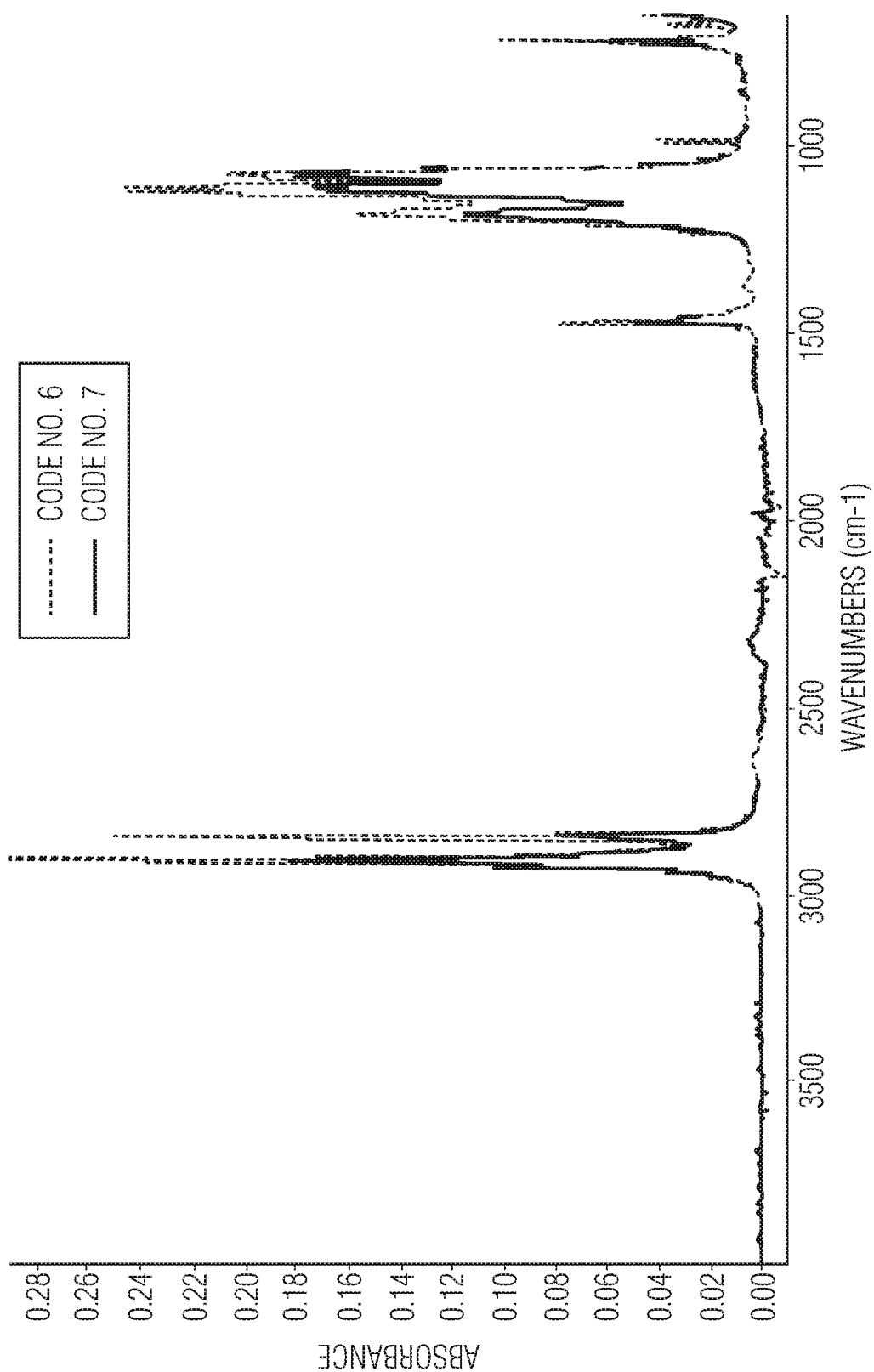
FIG. 13 is a graph depicting the IR spectra absorbance for the stretched film depicted in FIGS. 12A and 12B and the unstretched film depicted in FIGS. 11A and 11B.

The IR spectra absorbance for Code Nos. 6 and 7 is depicted in FIG. 13 and demonstrates similar IR spectra absorbance between the stretched film 12 including BaSO₄ particles 52 (Code No. 6) and the non-stretched film 12 including BaSO₄ particles 52 (Code No. 7). Stretching the film including BaSO₄ particles 52 (Code No. 6) was believed to create an oriented film and caused the PE band to increase in intensity. Specifically, a peak at 1100 cm$^{-1}$ is shown in FIG. 13 and an additional band at 1155 cm$^{-1}$ is shown as well.

Analysis of the SEM images described and illustrated herein was also conducted to determine the void volume and void size distribution for the codes of stretched and non-stretched films 12. Calculating the void volume and void size was completed by image analysis using ImageJ, an open source software that is Java-based and developed by the National Institutes of Health. Cross-sectional images from each sample were binarized such that film 12 material was white in the image and space created by the voids 50 were black. The void volume percentage was calculated based on the ratio of black pixel to total pixels in the image. The void size was calculated by inputting an ellipse in to each void and taking the average of the major and minor axis of the ellipse. The void volume percentage and the void size for each Code Nos. 1-7 are shown in Table 2. The void size distribution and frequency for Codes 1-7 are depicted graphically in FIG. 14.

TABLE 2

Void Volume and Void Size for Experimental Film Codes

| Code No. | Material | Stretch Ratio | Maximum Process Cut Speed (in/sec) | Void Volume % | Void Size (μm) Avg. | Max | Min |
|---|---|---|---|---|---|---|---|
| 1 | 60% LLDPE, 40% CaSO₄ | 300% | 300 | 8% | 0.73 | 7.08 | 0.33 |
| 2 | 60% LLDPE, 40% CaSO₄ | 0% | 175 | 3% | 0.30 | 2.18 | 0.10 |
| 3 | 49% LLDPE, 50% CaCO₃, 1% A-3000 (PTFE additive) | 450% | 325 | 9% | 0.58 | 4.84 | 0.01 |
| 4 | 50% LLDPE, 50% CaCO₃ | 450% | 300 | 13% | 0.94 | 7.64 | 0.32 |
| 5 | 50% LLDPE, 50% CaCO₃ | 0% | 125 | 2% | 0.35 | 3.53 | 0.10 |
| 6 | 60% LLDPE, 40% BaSO₄ | 400% | 275 | 2% | 0.57 | 2.56 | 0.34 |
| 7 | 60% LLDPE, 40% BaSO₄ | 0% | 350 | 1% | 0.30 | 2.20 | 0.10 |

Figure 14:
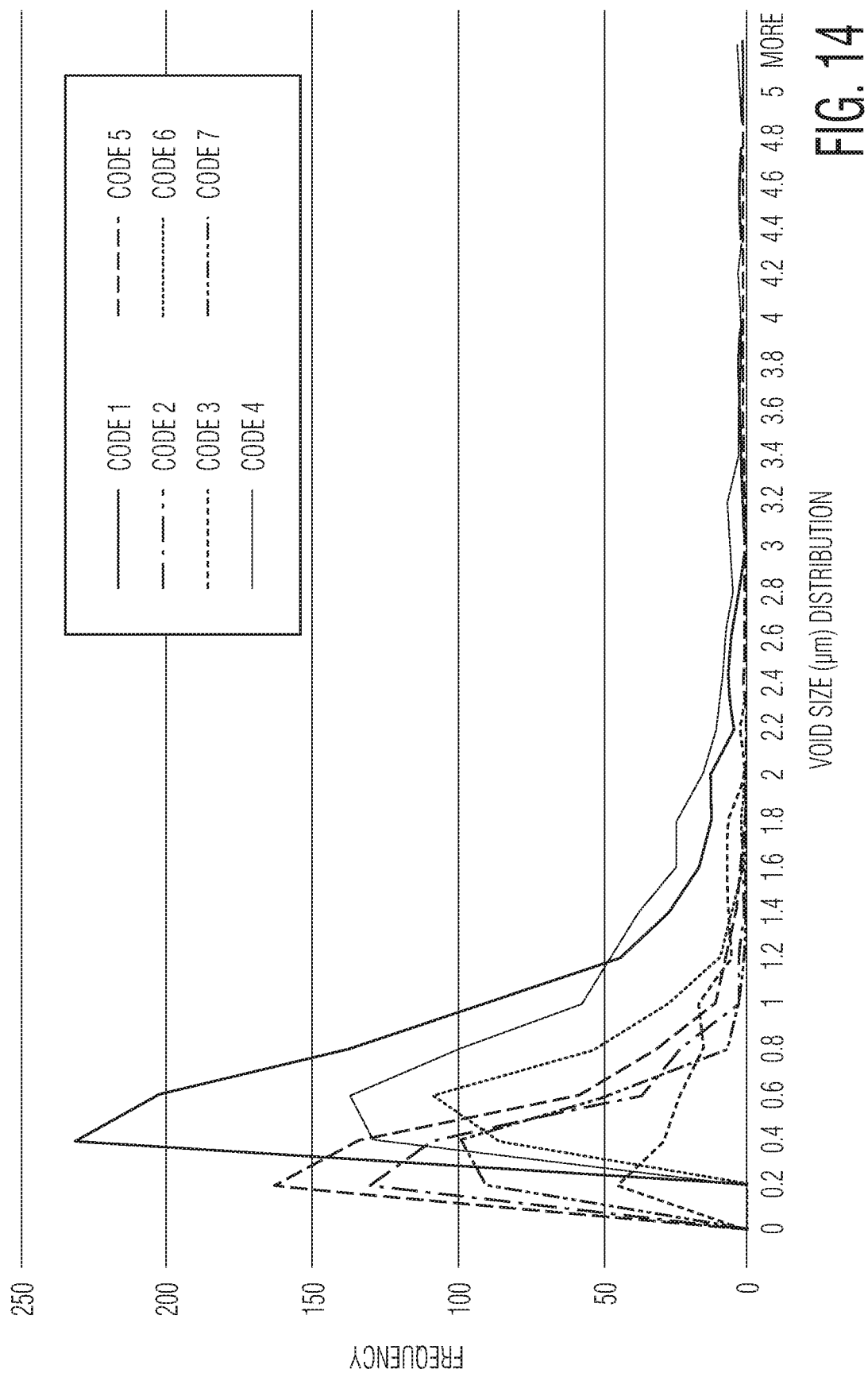
FIG. 14 is a graph depicting average void size distributions vs. frequency for the stretched films depicted in FIGS. 4A-5B, 9A, 9B, 12A, and 12B and for the unstretched films depicted in FIGS. 6A, 6B, 8A, 8B, 11A, and 11B.

As shown in Table 2 and FIG. 14, for the films 12 including CaSO₄ and CaCO₃ particles 52, the void volume percentage and the void size was significantly increased with stretching. However, there is very little change in the void volume percentage and the void size with stretching for the film 12 including BaSO₄ particles 52, which provide further explanation as to why the cutting speed did not increase after stretching for the film 12 including this particle 52.

Additional experimental film 12 codes were also created and tested utilizing particles 52 of calcium carbonate (CaCO₃) and barium phosphate (BaPO₄) and are shown in Table 3.

TABLE 3

Code Listing for Additional Experimental Films

| Code No. | Material | Stretch Rate | Maximum Process Cut Speed (in/sec) | Thickness (mils) |
|---|---|---|---|---|
| 8 | 100% LLDPE | 400% | 50 | 0.91 |
| 9 | 100% LLDPE | 0% | 25 | 0.75 |
| 10 | 50% LLDPE, 50% CaCO₃ | 300 | 250 | 1.02 |
| 11 | 50% LLDPE, 50% CaCO₃ | 0% | 125 | 0.59 |
| 12 | 50% LLDPE, 50% CaCO₃ | 500% | 275 | 0.63 |
| 13 | 50% LLDPE, 10% CaSO₄, 40% CaCO₃ | 0% | 150 | 0.71 |
| 14 | 50% LLDPE, 10% BaPO₄, 40% CaCO₃ | 300% | 550 | 1.26 |
| 15 | 50% LLDPE, 10% BaPO₄, 40% CaCO₃ | 0% | 400 | 0.55 |
| 16 | 60% LLDPE, 30% BaSO₄, 10% BaPO₄ | 350% | 550 | 0.83 |
| 17 | 60% LLDPE, 30% BaSO₄, 10% BaPO₄ | 0% | 400 | 0.55 |

Figure 15:
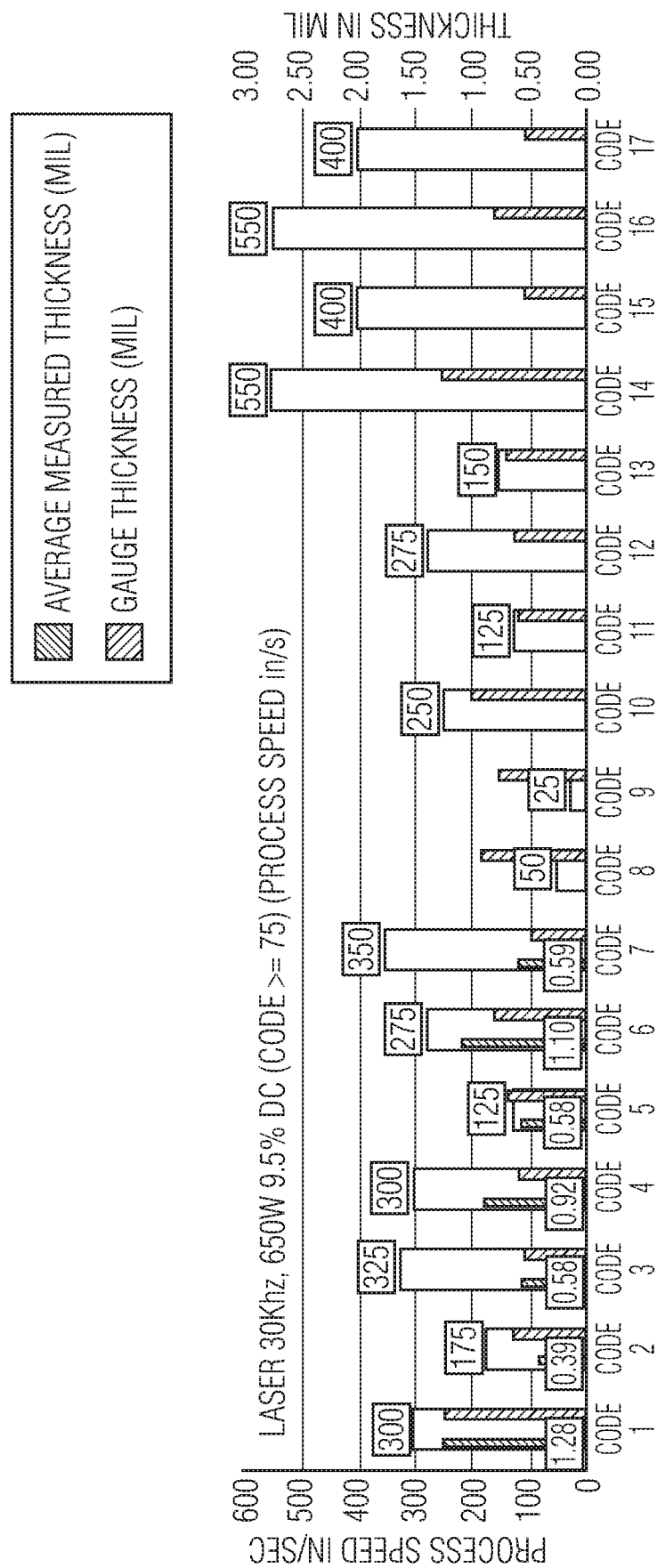
FIG. 15 is a graph depicting the laser cutting speed in comparison to the thickness for various exemplary codes.

FIG. 15 displays a graph showing the process speed and thickness for experimental films 12 of Codes 1-7 from Table 1 and Codes 8-17 from Table 3. As demonstrated from the results in FIG. 15 and Tables 1 and 3, providing particles 52 and stretching the film 12 typically enhances the cut speed. Combinations of different particles 52 may also be used in films 12 that are stretched and demonstrated enhanced cut speeds as well. Codes 14 and 16 demonstrated high cutting speeds as a result of the presence of voids 50 and particles 52.

Figure 16:
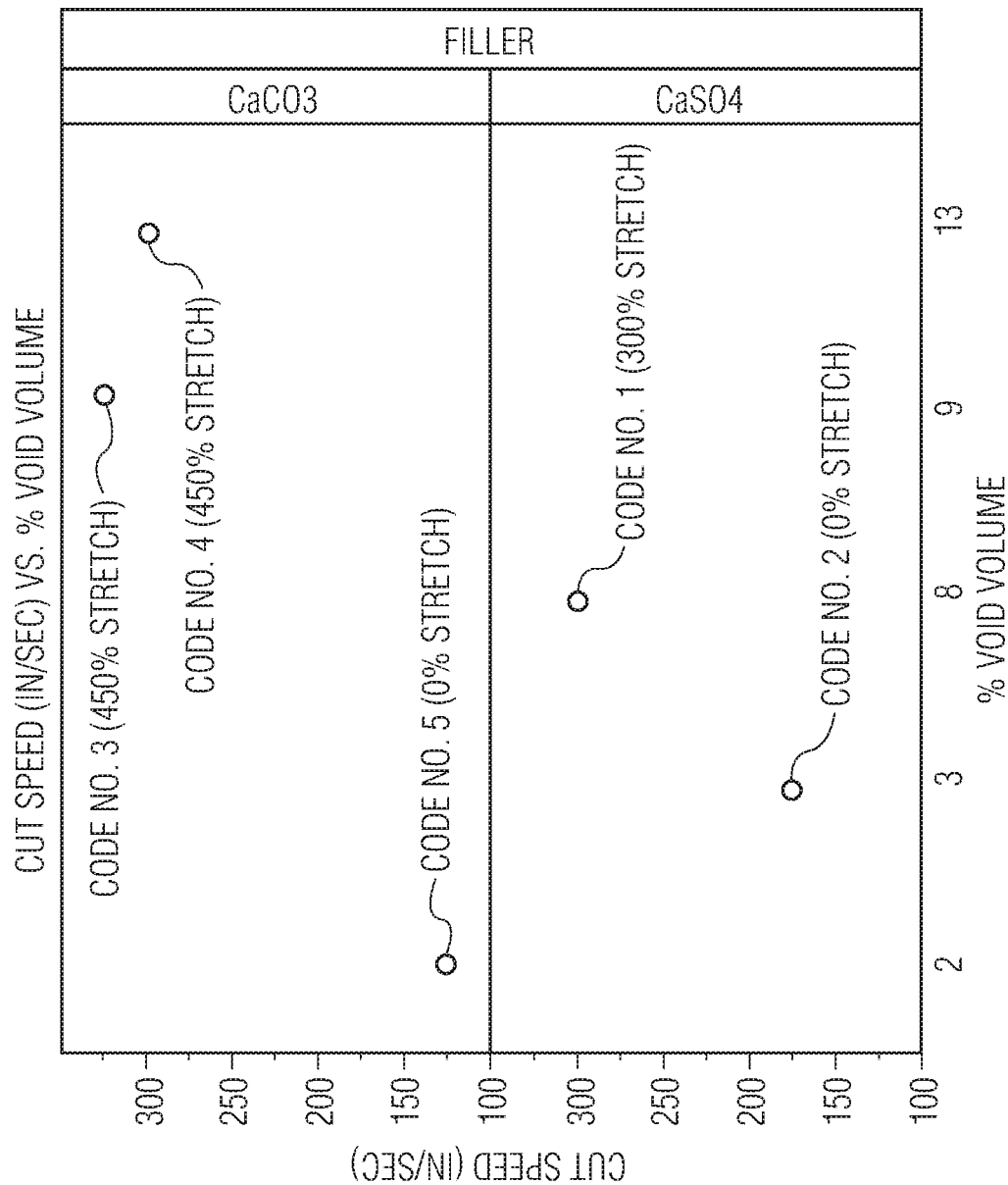
FIG. 16 is a graph depicting the laser cutting speed versus percentage of void volume for the films including filler particles of $CaCO_3$ as depicted in FIGS. 4A-6B and for the films including filler particles of $CaSO_4$ as depicted in FIGS. 8A-9B.
Figure 17:
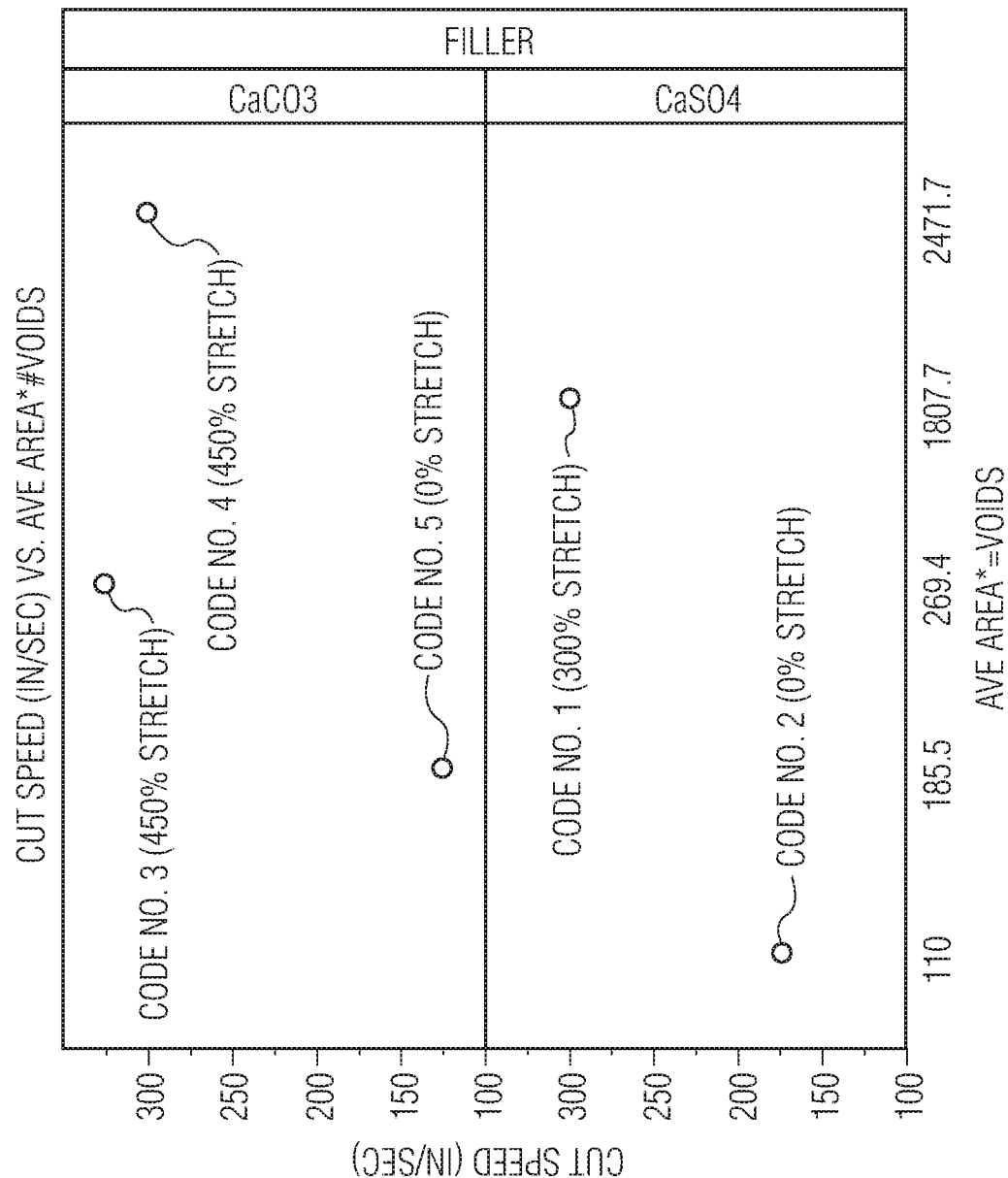
FIG. 17 is a graph depicting the laser cutting speed versus an estimated total void space calculated by the average void area multiplied by the quantity of voids for the films including filler particles of $CaCO_3$ as depicted in FIGS. 4A-6B and for the films including filler particles of $CaSO_4$ as depicted in FIGS. 8A-9B.

FIGS. 16 and 17 depict additional graphical analysis of cut speed against different variables for films 12 including particles of CaCO₃ and CaSO₄. FIG. 16 compares cut speed versus void volume percentage and FIG. 17 depicts cut speed versus the average area of voids multiplied by the number of voids, with FIGS. 16 and 17 also depicting the percentage stretch for each data point representing an experimental film 12. Additionally, FIG. 16 displays the trend that the greater the amount of stretch that is provided, the greater void volume percentage and increased cut speeds. FIG. 17 displays a similar trend in that the greater the amount of stretch provides a greater amount of void area, which leads to increased cut speeds, for films 12 that included CaCO₃ and CaSO₄ particles 52.

The solid state stretching of films 12 including particles 52 that provide for voids 50 to be created upon such stretching lead to higher cut speeds increasing manufacturing efficiency. Another benefit that is recognized by stretching of such films 12 is an improved edge softness of the polyolefin films 12, which may lead to improved comfort of products including such films 12, such as absorbent articles, as well as improved aesthetics.

EMBODIMENTS

Embodiment 1: A method for cutting or perforating a web, the method comprising: providing a web including a film, the film comprising: a polyolefin polymer; and a plurality of particles; the film including a width and a length defining a surface; stretching the film to provide a stretched film, wherein stretching the film provides a plurality of voids in the stretched film; providing a laser assembly; and directing a beam of light from the laser assembly upon the surface of the web to cut or perforate the web in at least one location.

Embodiment 2: The method of embodiment 1, wherein the plurality of voids provide a void volume percentage for the film, the void volume percentage being between about 2% to about 15%.

Embodiment 3: The method of embodiment 1 or 2, wherein the plurality of voids include an average size of about 0.30 □μm to about 2.00 μm.

Embodiment 4: The method of any one of the preceding embodiments, wherein the plurality of particles are selected from the group consisting of: carbon black, phosphates, phosphites, sulfates, sulfites, carbonates, polyvinyl butyral, mica, kaolinite, alumina, polyethylene terephthalate, and combinations thereof.

Embodiment 5: The method of any one of embodiments 1-3, wherein the plurality of particles are selected from the group consisting of: BaSO₄, BaPO₄, CaCO₃, CaSO₄, and combinations thereof.

Embodiment 6: The method of any one of the preceding embodiments, wherein the polyolefin polymer of the film comprises polyethylene, polypropylene, or a combination thereof.

Embodiment 7: The method of any one of the preceding embodiments, wherein the plurality of particles in the film provide a concentration of 10% to 60% of the film by total weight of the film.

Embodiment 8: The method of any one of the preceding embodiments, wherein stretching the film to provide the stretched film occurs prior to cutting the web.

Embodiment 9: The method of any one of the preceding embodiments, wherein the film is stretched at a percent stretch of between about 200% to about 500%.

Embodiment 10: The method of any one of the preceding embodiments, wherein the web further comprises a nonwoven.

Embodiment 11: The method of any one of the preceding embodiments, wherein the film forms a portion of an absorbent assembly for an absorbent article.

Embodiment 12: A method of cutting or perforating a web, the method comprising: providing a web including a film, the film comprising: a polyolefin polymer; and a plurality of particles; the film including a width in a film cross direction and a length in a film machine direction defining a surface; stretching the film in a stretch direction to provide a stretched film; providing a laser assembly; and directing a beam of light from the laser assembly upon the surface of the web with relative movement between the beam of light and the web to cut or perforate the web along a path, at least a first portion of the path is substantially parallel to the stretch direction.

Embodiment 13: The method of embodiment 12, wherein the stretch direction is the film machine direction.

Embodiment 14: The method of embodiment 12 or 13, wherein at least a second portion of the path is not substantially parallel to the stretch direction.

Embodiment 15: The method of embodiment 14, wherein at least a third portion of the path is substantially perpendicular to the stretch direction.

Embodiment 16: The method of any one of embodiments 12-15, wherein the web is stretched at a percent stretch of between about 200% to about 500%.

Embodiment 17: The method of any one of embodiments 12-16, wherein stretching the film in the stretch direction to provide the stretched web provides a plurality of voids in the film.

Embodiment 18: The method of embodiment 17, wherein the plurality of voids provide a void volume percentage for the film, the void volume percentage being between about 2% to about 15%.

Embodiment 19: The method of embodiment 17 or 18, wherein the plurality of voids include an average size of about 0.30 µm to about 2.00 µm.

Embodiment 20: The method of any one of embodiments 12-19, wherein the plurality of particles are selected from the group consisting of: carbon black, phosphates, phosphites, sulfates, sulfites, carbonates, polyvinyl butyral, mica, kaolinite, alumina, polyethylene terephthalate, and combinations thereof.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for cutting or perforating a web, the method comprising:
   providing a web including a film, the film comprising:
      a polyolefin polymer; and
      a plurality of particles;
      the film including a width and a length defining a surface;
   stretching the film to provide a stretched film, wherein stretching the film provides a plurality of voids in the stretched film, wherein the plurality of voids provide a void volume percentage for the stretched film greater than 5% and wherein the plurality of voids include an average size greater than 0.40 µm;
   providing a laser assembly; and
   directing a beam of light from the laser assembly upon the surface of the web to cut or perforate the web in at least one location.

2. The method of claim 1, wherein the void volume percentage is less than 15%.

3. The method of claim 1, wherein the average size is less than 2.00 µm.

4. The method of claim 1, wherein the plurality of particles are selected from the group consisting of: carbon black, phosphates, phosphites, sulfates, sulfites, carbonates, polyvinyl butyral, mica, kaolinite, alumina, polyethylene terephthalate, and combinations thereof.

5. The method of claim 1, wherein the plurality of particles are selected from the group consisting of: $BaSO_4$, $BaPO_4$, $CaCO_3$, $CaSO_4$, and combinations thereof.

6. The method of claim 1, wherein the polyolefin polymer of the film comprises polyethylene, polypropylene, or a combination thereof.

7. The method of claim 1, wherein the plurality of particles in the film provide a concentration of 10% to 60% of the film by total weight of the film.

8. The method of claim 1, wherein stretching the film to provide the stretched film occurs prior to cutting the web.

9. The method of claim 8, wherein the film is stretched at a percent stretch of between about 200% to about 500%.

10. The method of claim 1, wherein the web further comprises a nonwoven.

11. The method of claim 1, wherein the film forms a portion of an absorbent assembly for an absorbent article.

12. A method of cutting or perforating a web, the method comprising:
    providing a web including a film, the film comprising:
       a polyolefin polymer; and
       a plurality of particles;
       the film including a width in a film cross direction and a length in a film machine direction defining a surface;
    stretching the film in a stretch direction to provide a stretched film, wherein stretching the film in the stretch direction to provide the stretched web provides a plurality of voids in the film, wherein the plurality of voids provide a void volume percentage for the stretched film greater than 5% and wherein the plurality of voids include an average size greater than 0.40 µm;
    providing a laser assembly; and
    directing a beam of light from the laser assembly upon the surface of the web with relative movement between the beam of light and the web to cut or perforate the web along a path, at least a first portion of the path is substantially parallel to the stretch direction.

13. The method of claim 12, wherein the stretch direction is the film machine direction.

14. The method of claim 12, wherein at least a second portion of the path is not substantially parallel to the stretch direction.

15. The method of claim 14, wherein at least a third portion of the path is substantially perpendicular to the stretch direction.

16. The method of claim 12, wherein the web is stretched at a percent stretch of between about 200% to about 500%.

17. The method of claim 12, wherein the void volume percentage is less than 15%.

18. The method of claim 12, wherein the average size is less than 2.00 μm.

19. The method of claim 12, wherein the plurality of particles are selected from the group consisting of: carbon black, phosphates, phosphites, sulfates, sulfites, carbonates, polyvinyl butyral, mica, kaolinite, alumina, polyethylene terephthalate, and combinations thereof.

\* \* \* \* \*